(12) United States Patent
Sakaki et al.

(10) Patent No.: US 7,709,470 B2
(45) Date of Patent: May 4, 2010

(54) 11-PHENYL-DIBENZODIAZEPINE DERIVATIVES AS RXR-ANTAGONISTS

(75) Inventors: Junichi Sakaki, Ibaraki (JP); Kazuhide Konishi, Ibaraki (JP); Masashi Kishida, Ibaraki (JP); Masaaki Kimura, Ibaraki (JP); Hidefumi Uchiyama, Ibaraki (JP); Hironobu Mitani, Ibaraki (JP)

(73) Assignee: Novartis AG, Basel (CH)

( * ) Notice: Subject to any disclaimer, the term of this patent is extended or adjusted under 35 U.S.C. 154(b) by 927 days.

(21) Appl. No.: 10/550,776

(22) PCT Filed: Apr. 8, 2004

(86) PCT No.: PCT/EP2004/003806

§ 371 (c)(1),
(2), (4) Date: Jun. 20, 2006

(87) PCT Pub. No.: WO2004/089916

PCT Pub. Date: Oct. 21, 2004

(65) Prior Publication Data

US 2007/0043029 A1    Feb. 22, 2007

(30) Foreign Application Priority Data

Apr. 10, 2003   (GB)   .................................. 0308335.9

(51) Int. Cl.
*A61P 3/00*     (2006.01)
*A61K 31/551*   (2006.01)
*C07D 243/38*   (2006.01)

(52) U.S. Cl. .................... 514/219; 514/220; 540/555; 540/557

(58) Field of Classification Search ................. 514/219, 514/220; 540/555, 557
See application file for complete search history.

(56) References Cited

FOREIGN PATENT DOCUMENTS

| EP | 0 906 907 | 9/2000 |
|---|---|---|
| EP | 1 036 565 | 9/2005 |
| WO | WO 00/53562 | 9/2000 |
| WO | WO 02/072528 | 9/2002 |

OTHER PUBLICATIONS

Kagechika, H. et al., "Retinoid X Receptor-Antagonistic Diazepinylbenzoic Acids", Chem. Pharm. Bull., vol. 47, No. 12, pp. 1778-1786 (1999)*.

Umemiya, H. et al., "Regulation of Retinoidal Actions by Diazepinylbenzoic Acids. Retinoid Synergists which Activate the RXR-RAR Heterodimers", J. Med. Chem. vol. 40, 4222-4234 (1997).

*Primary Examiner*—Brenda L Coleman
(74) *Attorney, Agent, or Firm*—Theresa Devlin

(57) ABSTRACT

The present invention relates to novel benzodiazepine compounds exhibiting RXR-antagonist efficacy, for delaying progression of, preventing or treating a condition or disease being associated with RXR-antagonism, in particular selected from diabetes, complication of diabetes such as retinopathy, nephropathy, neuropathy, and hyperlipidemia, obesity, dyslipidemia, and osteoporosis.

10 Claims, No Drawings

11-PHENYL-DIBENZODIAZEPINE DERIVATIVES AS RXR-ANTAGONISTS

This application is a National Stage of International Application No. PCT/EP04/003806, filed on Apr. 8, 2004, which claims benefit under 35 U.S.C. §119(e) of Great Britain Application No. 0308335.9, filed on Apr. 10, 2003. The contents of both are incorporated herein by reference in their entirety.

Retiniod X receptors (RXRs) belong to the nuclear receptors superfamily and act as ligand-inducible transcriptional factors [Nagpal et al., Cell, 70: 1007-19 (1992); Kastner et al., Cell, 78:987-1003 (1995)]. RXRs regulate a wide variety of biological functions as a heterodimeric partner for other nuclear receptors, e.g., peroxisome proliferator-activated receptors (PPARs), liver X receptor (LXR), farnesoid X receptor (FXR) and retinoic acid receptors (RARs) [Mangelsdorf et al., Cell, 83:841-50 (1995)].

EP 906'907 (Institute of Medicinal Molecular Design, IMMD) describes certain benzodiazepine derivatives, such as HX531 and HX600, as compounds with an affinity to the retinoid X receptor. EP 906'9907 further teaches that the addressed compounds shall be in particular useful for the preventive or therapeutic treatments of vitamin A deficiency disease, hyperkeratosis of epithelial tissue, psoriasis, allergic diseases, immunological diseases such as rheumatism, bone diseases, leukemia, or cancers.

EP 1'036'565 (IMMD) describes similar benzodiazepines as in EP 906'907 which shall be useful for therapeutic and/or preventive treatment of: diabetes, the complications of diabetes such as retinopathy, nephropathy, neuropathy and hyperlipidemia, with reduced or no side effect such as hypoglycemic shock.

The present invention relates to novel benzodiazepine compounds exhibiting RXR-antagonist efficacy, to the manufacture and to the use of RXR antagonists. The class of RXR-antagonists, which have in particular the ability to reduce the body weight in an individual, for example, as exemplified in the KKA$^y$ in vivo mice model according to the present invention are represented by formula (I). Moreover, the RXR antagonists of the present invention may be useful in the delay of progression of, prevention of, and treatment of a disease or condition selected from the group consisting of diabetes; type-2-diabetes; diabetic complications such as retinopathy, nephropathy, neuropathy and hyperlipidemia; obesity; dyslipidemia; and osteoporosis.

The compounds of the present invention typically exhibit favorable pharmacological profile, e.g., an unexpected superior RXR-affinity, with a pronounced in vivo efficacy, e.g., in reducing effectively the body weight.

Accordingly, the present invention relates to benzodiazepine compounds of formula (I), or a pharmaceutically acceptable salt thereof,

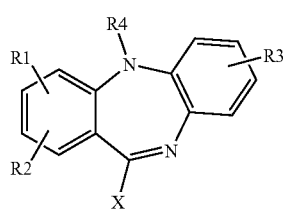

(I)

wherein $R_1$ and $R_2$, independently of each other, represent hydrogen, or $C_1$-$C_7$-alkyl, or $R_1$ and $R_2$ together with the carbon atoms of the phenyl ring to which they bind form a 5-, 6- or 7-membered cycloalkyl ring, which ring may optionally be substituted by one or more $C_1$-$C_7$-alkyl groups, which alkyl groups may also together form one or more 3-, 4-, 5-, 6- or 7-membered rings; $R_3$ represents —CN, —CO—$R_5$, or hydrogen, provided that, if $R_3$ is hydrogen, $R_4$ must represent $C_2$-$C_7$-alkenyl or $C_2$-$C_7$-alkynyl; $R_5$ represents aryl, or alkyl being unsubstituted or substituted by halogen, cyano, nitro, hydroxy, $C_1$-$C_7$-alkoxy, carboxyl or aryl; $R_4$ represents $C_1$-$C_7$-alkyl, $C_2$-$C_7$-alkenyl or $C_2$-$C_7$-alkynyl or $R_4$ represents $C_2$-$C_7$-alkanoyl; and X represents ligand (a),

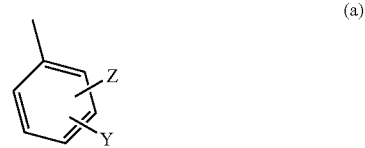

(a)

wherein Y may be in ortho, meta or para position and wherein Y represents carboxyl, $C_1$-$C_7$-alkoxycarbonyl, aryloxycarbonyl, tetrazolyl, $SO_3H$ or $P(O)(OH)_2$; and wherein Z represents hydrogen or a substituent selected from the group consisting of $C_1$-$C_7$-alkyl, $C_1$-$C_7$-alkoxy, halogen, $CF_3$, cyano, and $NO_2$.

The compounds of the present invention depending on the nature of the substituents may possess one or more asymmetric centers. The resulting diastereoisomers, optical isomers, i.e., enantiomers, and geometric isomers are encompassed by the instant invention.

Unless otherwise defined, the general terms used hereinabove and hereinbelow have the meanings given hereinbelow.

Alkyl as used herein has up to 14 carbon atoms, is linear, branched, cyclic or a combination thereof and is preferably $C_1$-$C_7$-alkyl, more preferably linear or branched $C_1$-$C_7$-alkyl, more specifically methyl, ethyl, n-propyl, isopropyl, cyclopropyl, methylcyclopropyl, cyclopropylmethyl, cyclobutyl, iso-butyl or tert-butyl. Alkyl is preferably $C_1$-$C_7$-alkyl.

$C_1$-$C_7$-Alkyl is preferably $C_1$-$C_5$-alkyl, most preferably $C_1$-$C_3$-alkyl and is in particular methyl, ethyl, n-propyl, and isopropyl, and especially methyl and ethyl.

$C_2$-$C_7$-Alkenyl is in particular $C_3$-$C_7$alkenyl and is, for example, 2-propenyl or 1-, 2- or 3-butenyl. $C_3$-$C_5$alkenyl is preferred, especially preferred is allyl.

$C_2$-$C_7$-Alkynyl is in particular $C_3$-$C_7$alkynyl and is preferably propargyl.

5-to 7-Membered cycloalkyl is, for example, cyclopropyl, cyclobutyl, cyclopentyl, cyclohexyl and cycloheptyl. Cyclopropyl, Cyclopentyl and cyclohexyl are preferred.

3-to 7-Membered rings, formed by $R_1$ and $R_2$ together with the carbon atoms of the phenyl ring to which they are attached, are, for example, represented by following partial structures:

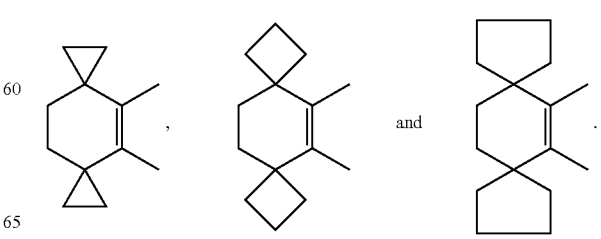

$C_1$-$C_7$-Alkoxy is, for example, $C_1$-$C_5$-alkoxy, preferably $C_1$-$C_3$-alkoxy, such as methoxy, ethoxy, propyloxy, isopropyloxy or butyloxy, but may also be isobutyloxy, sec-butyloxy, tert-butyloxy or a pentyloxy, hexyloxy or heptyloxy group. Preferred is methoxy and ethoxy.

As used herein halogen is preferably fluorine, chlorine, bromine, or iodine, more preferably fluorine, or chlorine, highly preferably fluorine.

As used herein, aryl stands for a carboxyclic aromatic moiety having from 6 to 14 carbon atoms, and is for example, phenyl or naphthyl or biphenylyl that is unsubstituted or substituted by $C_1$-$C_7$-alkyl, $C_1$-$C_7$-alkoxy, hydroxy, $C_1$-$C_7$-alkoxy-carbonyl, carboxy, carbamoyl, sulfamoyl, $C_2$-$C_7$-alkanoyl, halogen and/or by trifluoromethyl. Aryl as used herein stands also for an unsubstituted or substituted heteroaromatic radical optionally partially hydrogenated, 5- or 6-membered monocyclic heteroaryl or bicyclic heteroaryl composed of 5-or 6-membered rings, such as corresponding furyl, $C_1$-$C_7$-alkylfuryl, for example 4-methylfur-2-yl, thienyl, imidazolyl, for example imidazol-4-yl, oxazolyl, carboxy-$C_1$-$C_7$-alkyl(oxo)oxazolyl, for example 2,5-dihydro-3-oxo-1,2-oxazolyl, thiazolyl, dihydrothiazolyl, for example 4,5-dihydrothiazolyl, carboxy-$C_1$-$C_7$-alkylthiazolyl, for example 4-carboxymethylthiazolyl, $C_2$-$C_7$-alkoxycarbonyl-$C_1$-$C_7$-alkylthiazolyl, for example 4-methoxycarbonylmethylthiazolyl or 4-ethoxycarbonyl-methylthiazolyl, tetrazolyl, pyridyl, pyrazinyl, indolyl, for example indol-3-yl, quinolinyl, for example quinolin-4-yl, benzazepinyl or carboxy-$C_1$-$C_7$-alkyl-2,3,4,5-tetrahydro-1H-1-benzazepino, for example 1-carboxymethyl-2,3,4,5-tetrahydro-1H-1-benzazepino. Preferably, aryl is phenyl, pyridyl, thienyl or naphthyl that is unsubstituted or substituted by $C_1$-$C_7$-alkyl, $C_1$-$C_7$-alkoxy, hydroxy, carboxy, carbamoyl, sulfamoyl, $C_2$-$C_7$-alkanoyl, halogen and/or by trifluoromethyl. Representatives of corresponding heteroaryl comprise furyl, e.g. 2- or 3-furyl; thienyl, e.g. 2- or 3-thienyl; pyrrolyl, e.g. 1-, 2- or 3-pyrrolyl; oxazolyl, e.g. 2-, 4- or 5-oxazolyl, e.g. 2-, 4- or 5-oxazolyl; isoxazolyl, e.g. 3- or 4-isoxazolyl; imidazolyl, e.g. 2-, 4- or 5-imidazolyl; thiazolyl, e.g. 2-, 4- or 5-thiazolyl; isothiazolyl, e.g. 3- or 4-isothiazolyl; pyranyl, e.g. 2- or 3-pyranyl; pyridyl, e.g. 2- or 3-pyridyl; pyrazinyl, e.g. 3- or 4-pyrazinyl; pyrimidinyl, e.g. 2- or 4-pyrimidinyl; pyridazinyl, e.g. 2- or 3-pyridazinyl; tetrazoyl, e.g. tetrazol-5-yl. By the term "substituted by" the applicant means substituted by at least one of the listed substituents e.g. one, two, three or four substituents.

$C_2$-$C_7$-Alkoxycarbonyl is, for example, preferably $C_2$-$C_5$alkoxycarbonyl, such as methoxycarbonyl, ethoxycarbonyl, propyloxycarbonyl, isopropyloxycarbonyl or butyloxycarbonyl, but may also be isobutyloxycarbonyl, sec-butyloxycarbonyl, tert-butyloxy-carbonyl or a pentyloxycarbonyl, hexyloxycarbonyl or heptyloxycarbonyl group. Preferred is methoxy- or ethoxy-carbonyl.

Aryloxycarbonyl is, for example, phenyloxycarbonyl, naphthyloxycarbonyl such as 1- or 2-naphthyloxycarbonyl, or pyridyloxycarbonyl such as 2-, 3- or 4-pyridyloxycarbonyl.

$C_1$-$C_7$-Alkoxycarbonylcycloalkyl is, for example, $C_1$-$C_5$alkoxycarbonylcycloalkyl, preferably $C_1$-$C_3$-alkoxycarbonylcycloalkyl, such as methoxycarbonylcycloalkyl, ethoxycarbonyl-carbamoylcycloalkyl, propyloxycarbonylcycloalkyl, isopropyloxycarbonylcycloalkyl or butyloxycarbonylcycloalkyl, wherein cycloalkyl is, for example, cyclopropyl, cyclobutyl, cyclopentyl or cyclohexyl.

$C_2$-$C_7$-Alkoxycarbonyl-$C_1$-$C_7$-alkyl is, for example, $C_2$-$C_5$alkoxycarbonyl-$C_1$-$C_5$alkyl, preferably $C_2$-$C_3$alkoxycarbonyl-$C_1$-$C_3$alkyl, such as methoxycarbonylmethyl, methoxycarbonylethyl, ethoxycarbonylmethyl, ethoxycarbonylethyl, methoxycarbonylpropyl, ethoxycarbonylpropyl, propyloxycarbonylmethyl, propyloxycarbonylethyl, isopropyloxycarbonylmethyl, isopropyl-oxycarbonylethyl or butyloxycarbonylmethyl.

$C_2$-$C_7$-Alkoxycarbonyl-$C_1$-$C_7$-alkylene is, for example, $C_2$-$C_5$alkoxycarbonyl-$C_2$-$C_5$alkylene, preferably $C_2$-$C_3$alkoxycarbonyl-$C_2$-$C_3$alkylene, such as 1-methoxycarbonylethylene, 1-ethoxycarbonylethylene, 1,3-(methoxycarbonyl)propylene, 1,3-(ethoxycarbonyl)propylene, 1,3-(propyloxycarbonyl)propylene, 1,3-(butyloxycarbonyl)propylene, 1,3-(sec-butyl-oxycarbonyl)propylene or 1,3-(tert-butyloxycarbonyl)propylene.

$C_1$-$C_7$-Alkoxy-$C_1$-$C_7$-alkyl is, for example, $C_2$-$C_5$-alkoxy-$C_1$-$C_5$alkyl, such as 2-methoxyethyl, ethoxymethyl, 2-methoxyethyl, 2-ethoxyethyl, 3-methoxypropyl or 4-methoxybutyl.

$C_2$-$C_7$-Alkanoyl is, for example, $C_2$-$C_5$alkanoyl, preferably, $C_2$-$C_3$alkanoyl, such as acetyl, propionyl, butyryl, likewise pivaloyl. Most preferred is acetyl.

$R_1$ and $R_2$ independently represent hydrogen or a linear or branched $C_1$-$C_7$-alkyl group. As for the $C_1$-$C_7$-alkyl group, those mentioned above may be used, and ethyl group, isopropyl group, tert-butyl group or the like may preferably be used. The substituting positions of $R_1$ and $R_2$ are not particularly limited, and each of them may independently substitute at any position. However, it is preferred that $R_1$ and $R_2$ are at para-position and meta-position with reference to N—$R_4$, respectively, or $R_1$ and $R_2$ are at meta-position and ortho-position with reference to N—$R_4$. It is particularly preferred that $R_1$ and $R_2$ are at para-position and meta-position with reference to N—$R_4$, respectively. It is especially preferred that $R_1$ and $R_2$ are as illustrated in formula (IIa),

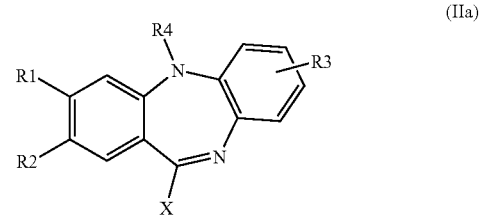

(IIa)

wherein $R_1$ and $R_2$ may combine to form a 5-, 6- or 7-membered cycloalkyl ring together with two carbon atoms on the phenyl ring to which $R_1$ and $R_2$ respectively bind. The cycloalkyl ring may have one or more $C_1$-$C_7$-alkyl groups, in particular $C_1$-$C_5$-alkyl. For example, such a cycloalkyl ring may have from two to four methyl groups, preferably four methyl groups. It is preferred that, for example, $R_1$ and $R_2$ together with the phenyl ring substituted with $R_1$ and $R_2$ form 5,6,7,8-tetrahydronaphthalene ring or 5,5,8,8-tetramethyl-5,6,7,8-tetrahydro-naphthalene ring, as illustrated in formula (IIc).

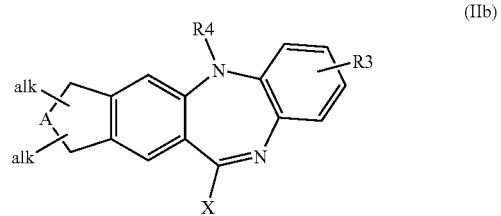

(IIb)

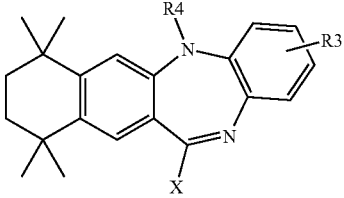
(IIc)

As exemplified in formula (IIb), $R_1$ and $R_2$ may form a 5-, 6- or 7-membered ring (A=$CH_2$, $CH_2CH_2$, or $CH_2CH_2CH_2$), preferably a 5- or 6-membered ring (A=$CH_2$, or $CH_2CH_2$), in particular a 6-membered ring, optionally substituted by one or more $C_1$-$C_7$-alkyl (alk=$C_1$-$C_7$-alkyl), which $C_1$-$C_7$-alkyl group may again combine with $C_1$-$C_7$-alkyl to represent a cycloalkyl ring, e.g., spirocyclic, such as cyclopropyl, cyclobutyl or cyclohexyl. In another preferred aspect said combined $C_1$-$C_7$-alkyl residues form a 3- to 7-membered cycloalkyl, especially cyclopropyl, preferably as illustrated in formula (IId),

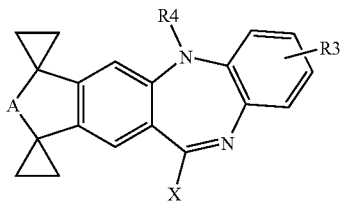
(IId)

wherein X represents preferably o-phenylene, m-phenylene, or p-phenylene substituted by Y. More preferably, X represents p-phenylene substituted by Y, as indicated in formula (b),

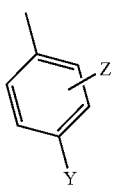
(b)

wherein Y represents preferably carboxyl, $C_1$-$C_7$-alkoxy-carbonyl, aryloxycarbonyl, tetrazolyl, $SO_3H$, more preferably carboxyl, tetrazolyl, especially tetrazol-5-yl, or $P(O)(OH)_2$, even more preferably carboxyl, or tetrazolyl, especially tetrazol-5-yl, in particular carboxyl. Y preferably is carboxy. Z is hydrogen or a substituent selected from the group consisting of $C_1$-$C_7$-alkyl, $C_1$-$C_7$-alkoxy, halogen, $CF_3$, cyano, and $NO_2$; especially preferred is halogen, most preferably fluorine.

Highly preferably, X represents p-carboxyl-phenyl.

$R_4$ represents $C_1$-$C_7$-alkyl, $C_3$-$C_7$-alkenyl or $C_3$-$C_7$-alkynyl. More preferably $R_4$ represents $C_1$-$C_5$-alkyl, even more preferably $C_1$-$C_3$-alkyl. In particular, $R_4$ is $CH_3$ or $C_2H_5$.

In another aspect $R_4$ represents $C_3$-$C_7$-alkenyl or $C_3$-$C_7$-alkynyl, provided $R_3$ represents hydrogen. A more preferred alkenyl is allyl. A preferred alkynyl is propargyl. Highly preferred substituents $R_4$ are allyl and propargyl, provided $R_3$ is hydrogen.

$R_3$ represents —CN, or —CO—$R_5$. $R_3$ may also represent hydrogen, provided however $R_4$ represents $C_3$-$C_7$-alkenyl or $C_3$-$C_7$-alkynyl. $R_5$ represents aryl, or alkyl being unsubstituted or substituted by halogen, cyano, nitro, hydroxy, $C_1$-$C_7$-alkoxy, carboxyl or aryl. Preferably $R_5$ represents $C_6$-$C_{14}$-aryl, or $C_1$-$C_{14}$-alkyl being unsubstituted or substituted by at least one substituent selected from halogen, cyano, nitro, hydroxy, $C_1$-$C_7$-alkoxy, carboxyl or $C_6$-$C_{14}$-aryl, such as one, two or three substituents.

The position of $R_3$ in the phenyl ring is not particularly limited, thus it may be at any position of the phenyl ring. A preferred position is the para-position relative to N—$R_4$ in general formula (I).

Preferred examples of the aryl moiety include phenyl, pyridyl, thienyl, naphthyl that is, in each case, unsubstituted or substituted by one or more, e.g. two, substituents selected from the group consisting of $C_1$-$C_7$-alkyl, $C_1$-$C_7$-alkoxy, hydroxy, carboxy, carbamoyl, sulfamoyl, $C_2$-$C_7$-alkanoyl, halogen and trifluoromethyl.

As for the alkyl group, $C_1$-$C_7$-alkyl is preferred, and the preferred examples may be used, in particular methyl, ethyl, propyl, butyl, isopropyl or the like.

Preferred examples of alkyl being substituted by halogen, cyano, nitro, hydroxy, alkoxy, or carboxyl include $C_1$-$C_7$-alkyl substituted by these and are, for example, fluoromethyl, fluoroethyl, difluoromethyl, trifluoromethyl, trichloroethyl, hydroxyethyl, hydroxypropyl, cyanomethyl, cyanoethyl, nitromethyl, methoxyethyl, and the like.

Preferred examples of the aryl moiety of the aryl-substituted alkyl group include, for example, phenyl, naphthyl, or pyridyl group, and the alkyl moiety may be either linear or branched and is preferably $C_1$-$C_7$-alkyl. For example, a phenyl-substituted $C_1$-$C_7$-alkyl group such as benzyl group or phenethyl group, a naphthyl-substituted $C_1$-$C_7$-alkyl group such as naphthylmethyl group, a pyridyl-substituted $C_1$-$C_7$-alkyl group such as pyridylmethyl group and the like can be used. The aryl group constituting these aryl-substituted $C_1$-$C_7$-alkyl groups may have one or more substituents. For example, a halogen atom such as fluorine atom or chlorine atom; a $C_1$-$C_7$-alkyl group such as methyl group or ethyl group; a linear or branched $C_1$-$C_7$-alkoxy group such as methoxy group or ethoxy group; nitro group; a cyano group, a linear or branched halogenated $C_1$-$C_7$-alkyl group such as trifluoromethyl group; hydroxyl group; carboxyl group; a $C_2$-$C_7$-alkoxycarbonyl group such as methoxycarbonyl.

More preferably $R_5$ represents methyl, ethyl, propyl, isopropyl, butyl, pentyl, hexyl, heptyl, phenyl, chlorophenyl, florophenyl, nitrophenyl, cyanophenyl, thienyl, pyridyl, benzyl, ethylphenyl, and the like.

Even more preferably, $R_3$ represents —CN, or —CO—$R_5$ wherein $R_5$ represents $C_1$-$C_7$-alkyl and in particular methyl, ethyl, propyl, isopropyl, butyl, pentyl, hexyl, heptyl. Highly preferably $R_3$ represents —CN, —CO-methyl, —CO-ethyl, —CO-propyl.

Preferred RXR-antagonists in accordance to the present invention are represented by formula (II c), wherein $R_3$ is hydrogen and $R_4$ is $C_3$-$C_7$-alkenyl or $C_3$-$C_7$-alkynyl; or $R_3$ is cyano; $C_2$-$C_7$-alkanoyl; or benzoyl which is unsubstituted or substituted by a substituent selected from the group consisting of $C_1$-$C_4$-alkyl, $C_1$-$C_4$-alkoxy, hydroxy, halogen and trifluoromethyl; and $R_4$ represents $C_1$-$C_4$alkyl, $C_3$-$C_7$-alkenyl, $C_3$-$C_7$-alkynyl, or $C_2$-$C_5$-alkanoyl; wherein X represents 4-carboxyphenyl, 2-halo-4-carboxypenyl or 3-halo-4-carboxyphenyl, especially 2-fluoro-4-carboxypenyl or 3-fluoro-4-carboxyphenyl.

Preferred RXR-antagonists in accordance to the present invention are represented by formula (IIc), wherein X represents 4-carboxy-phenyl; $R_3$ is cyano; and $R_4$ represents $C_1$-$C_7$-alkyl, $C_3$-$C_7$-alkenyl or $C_3$-$C_7$-alkynyl. A preferred position for $R_3$ is the para-position relative to N—$R_4$ in formula (IIc). In a more preferred aspect $R_4$ represents $C_1$-$C_7$-alkyl. In a even more preferred aspect, $R_3$ is cyano and is the para-position relative to N—$R_4$ in formula (IIc) and $R_4$ represents $C_1$-$C_7$-alkyl. $C_1$-$C_7$-Alkyl represents in this context even more preferably methyl or ethyl.

Further preferred RXR-antagonists in accordance to the present invention are represented by formula (IIe),

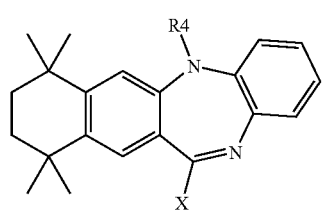

(IIe)

wherein X represents 4-carboxyphenyl; and $R_4$ represents $C_3$-$C_7$-alkenyl or $C_3$-$C_7$-alkynyl. A more preferred alkenyl is vinyl or allyl, in particular allyl. A preferred alkynyl is ethinyl or propargyl. Highly preferred substituents $R_4$ are allyl and propargyl.

Especially preferred is a compound of formula (IIc), or a salt thereof, wherein $R_3$ is hydrogen and $R_4$ is $C_3$-$C_7$-alkenyl, especially allyl, $C_3$-$C_7$-alkynyl, especially propargyl, or $C_3$-$C_7$-alkanoyl, especially acetyl; or $R_3$ is cyano or $C_2$-$C_5$-alkanoyl, especially acetyl; and $R_4$ is $C_1$-$C_4$-alkyl, especially methyl, ethyl, $C_3$-$C_5$-alkenyl, especially allyl, $C_3$-$C_5$-alkynyl, especially propargyl, or $C_2$-$C_5$-alkanoyl, especially acetyl; and X is 4-carboxy-phenyl and the phenyl ring is otherwise unsubstituted or substituted by halogen, especially fluorine, preferably in position 2 or 3 of the phenyl ring; for example, X is 4-carboxy-phenyl, 4-carboxy-3-fluoro-phenyl or 4-carboxy-2-fluoro-phenyl.

The compounds of formulae (IIIa), (IIIb), (IIIc), (IIId), (IIIe) and (IIIf) being disclosed infra, exhibit distinct RXR-antagonistic properties and are among the specifically preferred compounds:

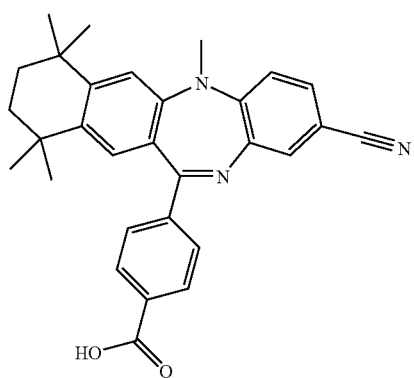

(IIIa)

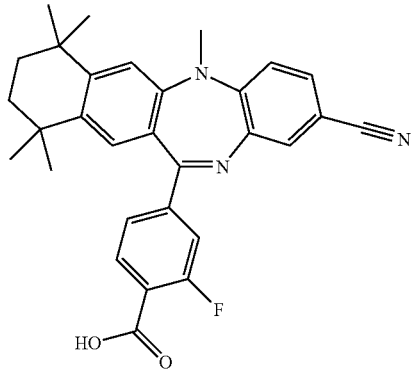

(IIIb)

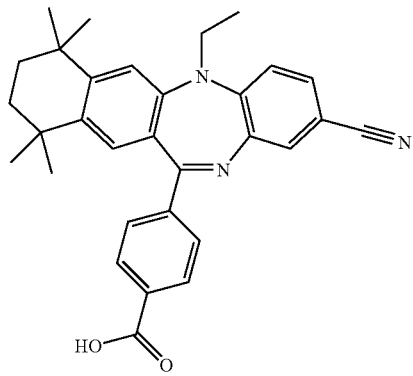

(IIIc)

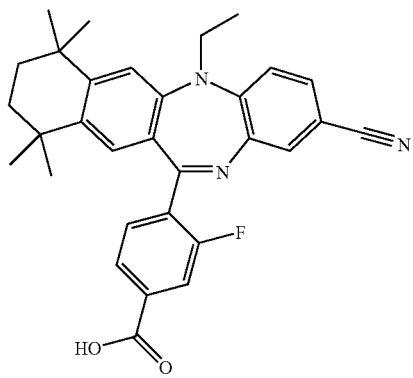

(IIId)

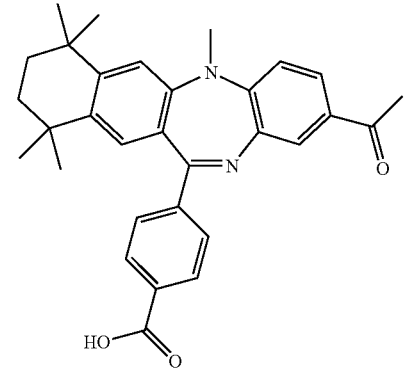

(IIIe)

-continued (IIIf)

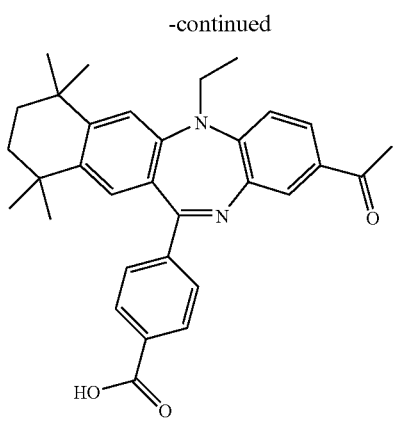

The present invention also pertains to a method of delaying progression of, preventing or treating a condition or disease being associated with RXR-antagonism, which method comprises the steps of administering an effective amount of a RXR antagonist, especially a compound of formula (I), or a more preferred compound selected from the compounds according to formulae (IIc), (IIe), (IIIa), (IIIb), (IIIc), (IIId), (IIIe) and (IIIf), or a salt thereof, to a patient in need of such treatment, wherein said condition or disease associated with RXR-antagonism is preferably selected from the group consisting of diabetes, type-2-diabetes, complication of diabetes such as retinopathy, nephropathy, neuropathy, and hyperlipidemia, obesity, dyslipidemia, and osteoporosis.

As used herein the terms "treatment", "treating" or "treat" refer to both prophylactic or preventive treatment as well as curative or disease-modifying treatment, including treatment of patients at risk of contracting the disease or suspected to have contracted the disease as well as patients who are ill or have been diagnosed as suffering from a disease or medical condition. Likewise, delay of progression of a condition or disease is comprised by the term "treatment" and the like.

The invention further pertains to the use of a compound according to formula (I), or a salt thereof, as a RXR-antagonist.

It also pertains to the use of a RXR-antagonist, in particular a compound of formula (I), or a salt thereof, in the manufacture of a medicament for delaying progression of, preventing or treating a condition or disease being associated with RXR-antagonism, in particular selected from diabetes, type-2-diabetes, complication of diabetes such as retinopathy, nephropathy, neuropathy, and hyperlipidemia, obesity, dyslipidemia, and osteoporosis.

The invention also pertains to a pharmaceutical composition comprising a RXR antagonist, especially a compound of the present invention, in particular of formula (I), in association with a pharmacologically and pharmaceutically acceptable additive.

The invention also pertains to a pharmaceutical composition for delaying progression of, preventing or treating a condition or disease being associated with RXR-antagonism, in particular selected from diabetes, type-2-diabetes, complication of diabetes such as retinopathy, nephropathy, neuropathy, and hyperlipidemia, obesity, dyslipidemia, and osteoporosis.

Compounds of formula (I) having acidic groups may form salts with bases. Compounds of formula (I) having basic groups may also form acid addition salts and, where in addition at least one acidic group is present, may also form internal salts.

Also included are both total and partial salts, that is to say salts with 1, 2 or 3, preferably 2, equivalents of base per mole of acid of formula (I), or salts with 1, 2 or 3 equivalents, preferably 1 equivalent, of acid per mole of base of formula (I).

For the purposes of isolation or purification it is also possible to use pharmaceutically unacceptable salts. Only the pharmaceutically acceptable, non-toxic salts (pharmaceutically acceptable salts) are used therapeutically and they are therefore preferred.

Combinations:

Another embodiment of the present invention relates to a combination, especially a pharmaceutical composition, comprising as active ingredients an RXR-antagonist, or a pharmaceutically acceptable salt thereof, especially a compound of formula (I) as described hereinbefore, and at least one other pharmaceutically effective drug selected from the group consisting of: diuretics, alpha-receptor blockers, beta-receptor antagonists, vasodilating agents, calcium antagonists, renin inhibitors, angiotensin II antagonists, angiotensin converting enzyme inhibitors (ACE-inhibitors), insulin secretion enhancers and insulin sensitizers.

Preferred combinations relate to a combination of (i) a RXR-antagonist, or a pharmaceutically acceptable-salt thereof, especially a compound of formula (I) as described hereinbefore; and (ii) at least one other active ingredient, selected from the group consisting of:

(a) $AT_1$-receptor antagonist, or a pharmaceutically acceptable salt thereof;

(b) an insulin secretion enhancer, or a pharmaceutically acceptable salt thereof; and (c) an insulin sensitizer, or a pharmaceutically acceptable salt thereof.

In case of a pharmaceutical composition, a pharmaceutically acceptable carrier is typically contained as well.

Preferably, the jointly therapeutically effective amounts of the active agents according to the combination of the present invention can be administered simultaneously or sequentially in any order, e.g., separately or in a fixed combination.

Under certain circumstances, drugs with different mechanisms of action may be combined. However, just considering any combination of drugs having different modes of action but acting in the similar field does not necessarily lead to combinations with advantageous effects.

A typical experimental finding of the present invention is that the combined administration of a RXR-antagonist and an $AT_1$ receptor antagonist and/or an insulin secretion enhancer and/or an insulin sensitizer, or, in each case, a pharmaceutically acceptable salt thereof, results not only in a beneficial, especially a potentiating or a synergistic, therapeutic efficacy.

Independent thereof, additional benefits resulting from combined treatment can be achieved such as a surprising prolongation of efficacy, a broader variety of therapeutic treatment and surprising beneficial effects on diseases and conditions associated with diabetes and obesity, e.g., less gain of weight. An additional and preferred aspect of the present invention is the prevention, delay of progression or treatment of the condition of isolated systolic hypertension and impaired vascular compliance which means decreased vascular elasticity.

The term "potentiation" shall mean an increase of a corresponding pharmacological efficacy or therapeutical effect, respectively. Potentiation of one component of the combination according to the present invention by co-administration of an other component according to the present invention means that an effect is being achieved that is greater than that achieved with one component alone.

The term "synergistic" shall mean that the drugs, when taken together, produce a total joint effect which is greater than the sum of the effects of each drug when taken alone.

As used herein, $AT_1$-receptor antagonists (also called angiotensin II receptor antagonists or blockers) bind to the $AT_1$-receptor subtype of angiotensin II receptor but do not result in activation of the receptor. As a consequence of the blockade of the $AT_1$ receptor, these antagonists can, for example, be employed as antihypertensives or for treating congestive heart failure.

The class of $AT_1$ receptor antagonists comprises compounds having differing structural features, essentially preferred are the non-peptidic ones. Typically such compounds are selected from the group consisting of valsartan (cf. EP 443'983), losartan (cf. EP 253'310), candesartan (cf. EP 459'136), eprosartan (cf. EP 403'159), irbesartan (cf. EP 454'511), olmesartan (cf. U.S. Pat. No. 5,616,599), tasosartan (cf. EP 539'086), and telmisartan (cf. EP 502'314), or, in each case, a pharmaceutically acceptable salt thereof.

Preferred $AT_1$-receptor antagonist are those agents that have been marketed, most preferred is valsartan, or a pharmaceutically acceptable salt thereof.

A preferred renin inhibitor is aliskiren, or a pharmaceutically acceptable salt thereof.

A preferred ACE-inhibitor is, for example, enalapril or enalaprilate, benazepril or benazeprilate, lisinopril or ramipril or, in each case, a pharmaceutically acceptable salt thereof.

Insulin secretion enhancers are active ingredients that have the property to promote the secretion of insulin from pancreatic β-cells. Examples of insulin secretion enhancers are sulfonylureas (SU), especially those which promote the secretion of insulin from pancreatic β-cells by transmitting signals of insulin secretion via SU receptors in the cell membrane, including, but not limited to, tolbutamide; chlorpropamide; tolazamide; acetohexamide; 4-chloro-N-[(1-pyrolidinylamino)carbonyl]-benzensulfonamide (glycopyramide); glibenclamide (glyburide); gliclazide; 1-butyl-3-metanilylurea; carbutamide; glibonuride; glipizide; gliquidone; glisoxepid; glybuthiazole; glibuzole; glyhexamide; glymidine; glypinamide; phenbutamide; and tolylcyclamide, or a pharmaceutically acceptable salt thereof.

Insulin secretion enhancers furthermore include short-acting insulin secretion enhancers, such as the new phenylalanine derivative nateglinide [N-(trans-4-isopropylcyclohexylcarbonyl)-D-phenylalanine] (cf. EP 196'222 and EP 526'171) of the formula

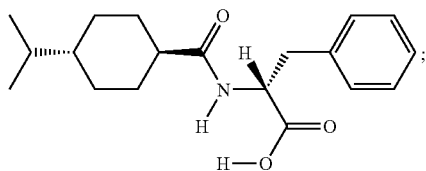

repaglinide [(S)-2-ethoxy-4-{2-[[3-methyl-1-[2-(1-piperidinyl)phenyl]butyl]amino]-2-oxoethyl}benzoic acid—cf. EP 589'874]; calcium (2S)-2-benzyl-3-(cis-hexahydro-2-isoindolinlycarbonyl)-propionate dihydrate (mitiglinide—cf. EP 507'534); furthermore representatives of the new generation of SUs such as glimepiride (cf. EP 31'058); and in free or pharmaceutically acceptable salt form.

As used herein, insulin secretion enhancers include the long-acting insulin secretion enhancer DPP-IV inhibitors, GLP-1 and GLP-1 agonists.

DPP-IV is responsible for inactivating GLP-1. More particularly, DPP-IV generates a GLP-1 receptor antagonist and thereby shortens the physiological response to GLP-1. GLP-1 is a major stimulator of pancreatic insulin secretion and has direct beneficial effects on glucose disposal.

The DPP-IV inhibitor can be peptidic or, preferably, non-peptidic. DPP-IV inhibitors are in each case generically and specifically disclosed, e.g., in WO 98/19998, DE 196 16 486 A1, WO 00/34241 and WO 95/15309, in each case in particular in the compound claims and the final products of the working examples, the subject-matter of the final products, the pharmaceutical preparations and the claims are hereby incorporated into the present application by reference to these publications. Preferred are those compounds that are specifically disclosed in Example 3 of WO 98/19998 and Example 1 of WO 00/34241, respectively.

GLP-1 is a insulinotropic protein which was described, e.g., by W. E. Schmidt et al. in Diabetologia 28, 1985, 704-707 and in U.S. Pat. No. 5,705,483.

The term "GLP-1 agonists" used herein means variants and analogs of GLP-1(7-36)$NH_2$ which are disclosed in particular in U.S. Pat. No. 5,120,712, U.S. Pat. No. 5,118,666, U.S. Pat. No. 5,512,549, WO 91/11457 and by C. Orskov et al in J. Biol. Chem. 264 (1989) 12826. The term "GLP-1 agonists" comprises especially compounds like GLP-1(7-37), in which compound the carboxy-terminal amide functionality of $Arg^{36}$ is displaced with Gly at the $37^{th}$ position of the GLP-1(7-36) $NH_2$ molecule and variants and analogs thereof including $GLN^9$-GLP-1(7-37), D-$GLN^9$-GLP-1(7-37), acetyl $LYS^9$-GLP-1(7-37), $LYS^{18}$-GLP-1(7-37) and, in particular, GLP-1(7-37)OH, $VAL^8$-GLP-1(7-37), $GLY^8$-GLP-1(7-37), $THR^8$-GLP-1(7-37), $MET^8$-GLP-1(7-37) and 4-imidazopropionyl-GLP-1. Special preference is also given to the GLP agonist analog exendin-4, described by Greig et al in Diabetologia 42, 1999, 45-50.

A preferred insulin secretion enhancer is repaglinide, most preferred is nateglinide.

The term nateglinide likewise comprises crystal modifications such as disclosed in EP 526'171 or U.S. Pat. No. 5,488, 510, respectively, the subject matter of which, especially with respect to the identification, manufacture and characterization of crystal modifications, is herewith incorporated by reference to this application, especially the subject matter of claims 8 to 10 (being directed to the H-form crystal modification) as well as the corresponding references to the B-form crystal modification.

The structure of the active agents identified by generic or tradenames may be taken from the actual edition of the standard compendium "The Merck Index" or from databases, e.g., Patents International (e.g. IMS World Publications). The corresponding content thereof is hereby incorporated by reference. Any person skilled in the art is fully enabled to identify the active agents and, based on these references, likewise enabled to manufacture and test the pharmaceutical indications and properties in standard test models, both in vitro and in vivo.

The term "short-acting insulin secretion enhancer" comprises corresponding agents with a maximum secretion of insulin that is attained within one hour, preferably within 30 min, after the administration of the agent, most preferably within 20 min having a biological half-life, $T_{1/2}$, of less than two h, preferably, 1.5 h. The term long-acting insulin secretion enhancer" comprises corresponding agents with a maximum secretion of insulin that is attained more than one hour after administration of the agent.

A preferred insulin sensitizer is metformin or a pharmaceutically acceptable salt thereof such as the mono-hydrochloride.

Especially preferred is a combination of a preferred RXR-antagonist of the present invention with valsartan or a pharmaceutically acceptable salt thereof and/or nateglinide or a pharmaceutically acceptable salt thereof.

The corresponding active ingredients or a pharmaceutically acceptable salts thereof may also be used in form of a solvate, such as a hydrate or including other solvents, used for crystallization.

The compounds to be combined can be present as pharmaceutically acceptable salts. If these compounds have, for example, at least one basic center, they can form acid addition salts. Corresponding acid addition salts can also be formed having, if desired, an additionally present basic center. The compounds having an acid group (for example COOH) can also form salts with bases.

The pharmaceutical activities as effected by administration of representatives of the class of RXR-antagonists of formula (I), or $AT_1$-receptor antagonists or insulin secretion enhancers, respectively, or of the combination of active agents used according to the present invention can be demonstrated, e.g., by using corresponding pharmacological models known in the pertinent art. The person skilled in the pertinent art is fully enabled to select a relevant animal test model to prove the hereinbefore and hereinafter indicated therapeutic indications and beneficial effects.

Experimental Part—Biology

1) In vitro Model: Reporter Gene Assay

To determine the effects of an RXR-antagonist at the cellular level, a reporter gene assay is used to assess gene expression and regulation by an antagonist. A reporter gene assay for RXRα homodimer is performed using 9-cis-retinoic acid and LG100268, RXR selective ligand. HEK 293 cells are transfected with the hRXRα expression vector, pcDNA-hRXRα and reporter plasmid, pGL3proCRBPII. For assays, the cells are seeded in 96 well issue culture plates. The next day, 9-cis-retinoic acid or LG100268 as the activating ligand are added to the medium in the presence or absence of RXR antagonists. After 20-24 h incubation, the cells are lysed and the luciferase activity is measured.

2) In vivo Model: KKA$^y$ Mice

KKA$^y$ mice [Iwatsuka et al., Endocrinol. Jpn., 17: 23-35 (1970)] are characterized by severe obesity and features of type 2 diabetes [Herberg et al., Metabolism, 26: 59-99, 1970, Hayase et al., Am. J. Physiol., 271: E333-9, 1996]. This animal model is useful to study the pathogenesis, therapy, and prevention of obesity and diabetes.

The efficacy of RXR-antagonists is determined in obese diabetic KKA$^y$ mice using similar method described by Yamauchi et al. [J. Clin. Invest., 108: 1001-13, 2001]. Male 8-9 week old KKA$^y$ mice pre-fed a high fat diet for 1-2 weeks are divided into the groups. RXR antagonists are administered as a food admixture for 1-2 weeks. Body weight and food intake are monitored during the administration. After the administration, blood samples are taken and the heparinized plasma samples are stored at −80° C. after the centrifugation (4° C., 1,500 times g, 10 min) for the measurement of plasma parameters. The parameters are measured using commercially available kits.

Highly preferred compounds so far based on the data observed in the in vivo KKA$^y$ screening are the compounds of formula (IIIa), (IIIb), (IIIc), (IIId), (IIIe) and (IIIf).

3) In vitro Model: RXRα Binding Assay

Varying concentrations of $^3$H 9-cis-RA (retinoic acid) are incubated with or without 50 ng of full length glutathione-S-transferase (GST)-human RXRα for 18 h at 4° C. 200 micro liter binding buffer under continuous rotation. After addition of 80 micro liter of 20% hydroxyapatite (HA) slurry, reaction tubes are further incubated for 15 min at 4° C., and then, centrifuged for 2 min at 15,000 g-force. Collected HA is washed with 250 micro liter of buffer 3 times, re-suspended 250 micro liter ethanol, and then transferred to a vial containing 5 mL of scintillate to measure radioactivity. Competitive binding assay: The competitive binding assay is carried out by using 20 tm of $^3$H 9-cis-RA in the absence (100% binding) or presence of increasing concentrations ($10^{-10}$~$10^{-4}$ M) of, e.g., HX531.

Experimental Part—Pharmacology

As used herein, pharmaceutical preparations are for enteral, such as oral, and also rectal or parenteral, administration to homeotherms, with the preparations comprising the pharmacological active compound either alone or together with customary pharmaceutical auxiliary substances. For example, the pharmaceutical preparations consist of from about 0.1% to 90%, preferably of from about 1% to about 80%, of the active compound. Pharmaceutical preparations for enteral or parenteral, and also for topical, e.g., ocular, administration are, for example, in unit dose forms, such as coated tablets, tablets, capsules or suppositories and also ampoules. These are prepared in a manner that is known per se, for example using conventional mixing, granulation, coating, solubilizing or lyophilizing processes. Thus, pharmaceutical preparations for oral use can be obtained by combining the active compound with solid excipients, if desired granulating a mixture which has been obtained, and, if required or necessary, processing the mixture or granulate into tablets or coated tablet cores after having added suitable auxiliary substances.

The aforementioned pharmaceutical compositions may be prepared by the addition of pharmacologically and pharmaceutically acceptable additives. Examples of pharmacologically and pharmaceutically acceptable additives include, for example, excipients, disintegrators and disintegrating aids, binders, lubricants, coating agents, colorants, diluents, base materials, dissolving agents and dissolving aids, isotonic agents, pH modifiers, stabilizers, propellants, adhesives and the like.

The dosage of the active compound can depend on a variety of factors, such as mode of administration, homeothermic (warm blooded) species, age and/or individual condition.

Preferred dosages for the active ingredients of the pharmaceutical combination according to the present invention are therapeutically effective dosages, especially those which are commercially available.

Normally, in the case of oral administration, an approximate daily dose of from about 0.01 mg to about 1000 mg is to be estimated e.g. for a patient of approximately 75 kg in weight.

Typically, a representative of an RXR-antagonist of formula (I), will be supplied in the form of suitable dosage unit form, for example, a capsule or tablet, and comprising a therapeutically effective amount, e.g. from about 20 to about 320 mg, which may be applied to patients. The application of the active ingredient may occur up to three times a day, starting, e.g., with a daily dose of 20 mg or 40 mg of active ingredient, increasing via 80 mg daily and further to 160 mg daily up to 320 mg daily. Preferably, active ingredient is applied twice a day with a dose of 80 mg or 160 mg, respectively, each. In a low-dose formulation, active ingredient with a dose of 20 mg or 40 mg may be used. Corresponding doses may be taken, for example, in the morning, at mid-day or in the evening. Preferred is b.i.d. administration.

The next paragraphs describe representative galenic formulations, comprising typically a pharmaceutically effective amount of a compound of formula (I).

Tablets:

Tablets, each comprising 50 mg of active ingredient according to the definition of formula (I) or a salt thereof, can be prepared as follows:

Composition (10 000 Tablets)

| | |
|---|---|
| active ingredient | 500.0 g |
| lactose | 500.0 g |
| potato starch | 352.0 g |
| gelatin | 8.0 g |
| talc | 60.0 g |
| magnesium stearate | 10.0 g |
| silicon dioxide (highly dispersed) | 20.0 g |
| ethanol | q.s. |

The active ingredient is mixed with the lactose and 292 g of potato starch and the mixture is moistened with an ethanolic solution of the gelatin and granulated through a sieve. After drying, the remainder of the potato starch, the magnesium stearate, the talc and the silicon dioxide are mixed in and the mixture is compressed to form tablets, each weighing 145.0 mg and comprising 50.0 mg of active ingredient; the tablets may, if desired, be provided with breaking notches for finer adaptation of the dose.

Sterile Solution:

A sterile-filtered aqueous gelatin solution which comprises 20% cyclodextrins as solubiliser and which comprises 3 mg of an active ingredient in accordance to this invention or of a salt, for example the sodium salt, thereof as active ingredient, is mixed under aseptic conditions, with heating, with a sterile gelatin solution that comprises phenol as preservative in such a manner that 1.0 mL of solution has the following composition:

| | |
|---|---|
| active ingredient | 3 mg |
| gelatin | 150.0 mg |

-continued

| | |
|---|---|
| phenol | 4.7 mg |
| dist. water with 20% cyclodextrins as solubilizer | 1.0 mL |

Sterile Dry Substance for Injection:

5 mg of one of the compounds of formula I mentioned in the working Examples as active ingredient are dissolved in 1 mL of an aqueous solution comprising 20 mg of mannitol and 20% cyclodextrins as solubiliser. The solution is sterile-filtered and introduced under aseptic conditions into a 2 mL ampoule, is deep-frozen and lyophilised. Before use, the lyophilisate is dissolved in 1 mL of distilled water or 1 mL of physiological saline solution. The solution is administered intramuscularly or intravenously. This formulation can also be introduced into double-chamber injection ampoules.

Film Coated Tablets:

10 000 film-coated tablets, each comprising 100 mg of an active ingredient in accordance to this invention can be prepared as follows:

| | |
|---|---|
| active ingredient | 1000 g |
| corn starch | 680 g |
| colloidal silicic acid | 200 g |
| magnesium stearate | 20 g |
| stearic acid | 50 g |
| sodium carboxy-methyl starch | 250 g |
| water | q.s. |

A mixture of one of the compounds of formula (I), e.g., as mentioned in the working Examples as active ingredient, 50 g of corn starch and the colloidal silicic acid is processed with starch paste consisting of 250 g of corn starch and 2.2 kg of demineralised water to form a moist mass. The moist mass is forced through a sieve having a mesh size of 3 mm and is dried at 45° C. for 30 min in a fluidized bed dryer. The dried granules are pressed through a sieve having a mesh size of 1 mm, are mixed with a previously sieved mixture (1 mm sieve) of 330 g of corn starch, the magnesium stearate, the stearic acid and the sodium carboxymethyl starch, and are compressed to form slightly biconvex tablets.

In a manner analogous to that described above, it is also possible to prepare pharmaceutical preparations comprising a different compound according to any one of Experimental Part—Chemistry.

Experimental Part—Chemistry

The compounds of formula (I) can be prepared, for example, as described in the following reaction schemes and in the working examples.

REFERENTIAL EXAMPLES

Synthesis of Monosubstituted Terephthalic Acid Monomethyl Ester

The monosubstituted terephthalic acid monomethyl esters which were used in the foregoing examples as the raw materials may be synthesized as described in the following paragraphs.

Reaction scheme 1:
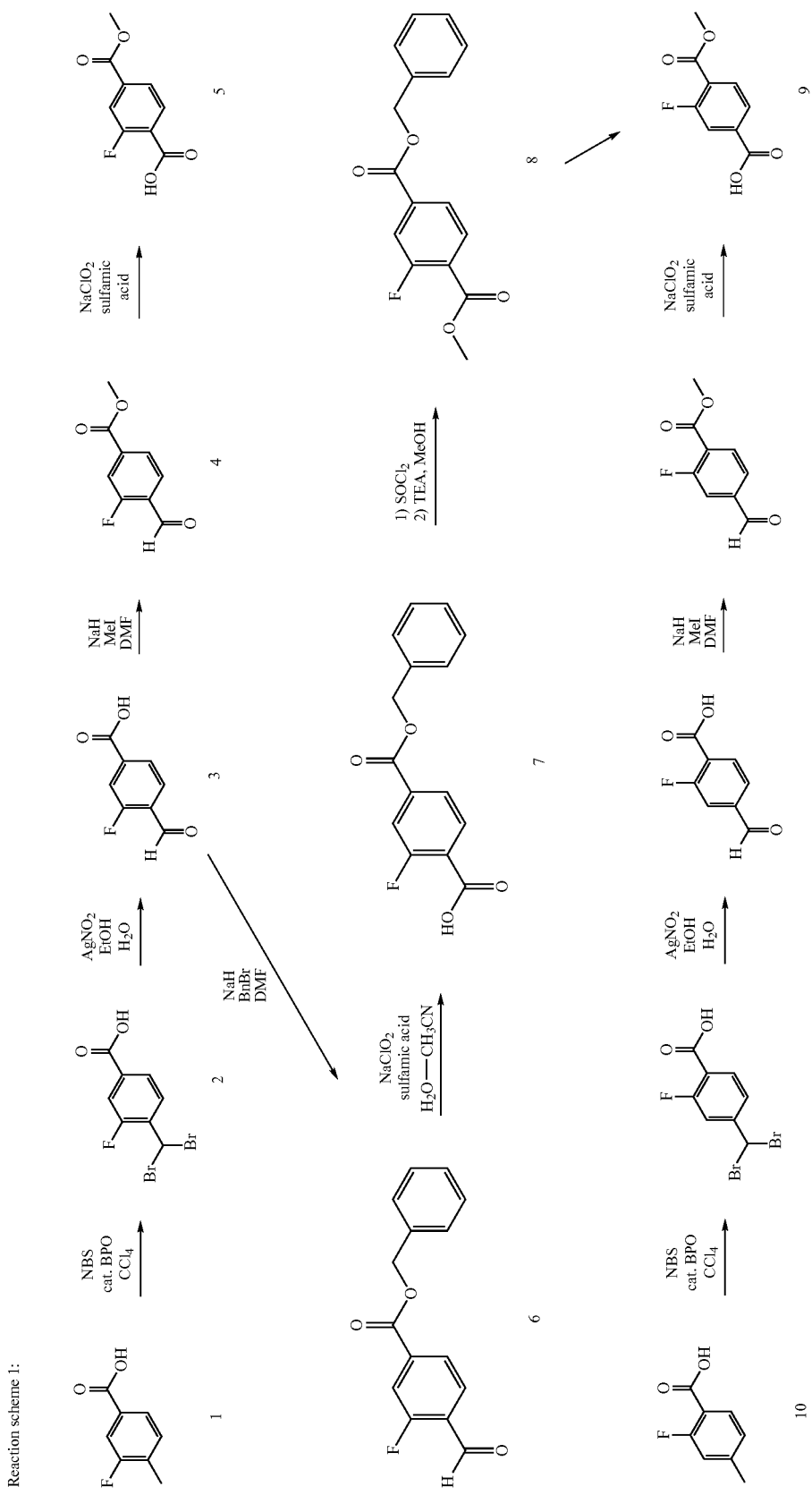

4-Dibromomethyl-3-fluorobenzoic Acid (2)

A solution of 3-fluoro-4-methyl benzoic acid (1, 0.19 mol), N-bromosuccinimide (0.45 mol) and benzoyl peroxide (9.1 mmol) in $CCl_4$ (360 mL) is refluxed for 36 h. The reaction mixture is cooled to room temperature and filtered off. The residue is washed with $CCl_4$ and the combined filtrates are concentrated to give crude 4-dibromomethyl-3-fluorobenzoic acid (2).

3-Fluoro-4-formyl Benzoic Acid (3)

$AgNO_3$ (0.39 mol) in hot $H_2O$ (90 mL) is added dropwise to a solution of crude 4-dibromomethyl-3-fluorobenzoic acid (2, 0.19 mol) in ethanol (EtOH) (480 mL) at 50° C. over 10 min and then the mixture is stirred at the same temperature for 45 min. After cooling to room temperature, the mixture is poured into 1 N HCl (200 mL) and filtered off. The residue is washed with EtOH and the filtrate is concentrated to ca. 300 mL. The mixture is extracted twice with ethylacetate (EtOAc) and the combined organic layers are washed with brine, dried over $MgSO_4$ and evaporated in vacuo. The crystals are collected by filtration and washed with ether/hexane (1:1) to give 3-fluoro-4-formyl benzoic acid (3).

3-Fluoro-4-formyl Benzoic Acid Methyl Ester (4)

60% NaH (0.14 mol) is added portionwise to a solution of 3-fluoro-4-formyl benzoic acid (3, 0.12 mol) in dry DMF (330 mL). The mixture is stirred at room temperature for 30 min. Methyl iodide (0.14 mol) is added dropwise to the mixture. After stirring at room temperature for 5 h, the reaction mixture is poured into 1 N HCl (ca. 1000 mL) and extracted twice with EtOAc. The combined organic layers are washed with saturated aqueous $NaHCO_3$, brine, dried over $MgSO_4$, and evaporated in vacuo to give crude 3-fluoro-4-formyl benzoic acid methyl ester (4).

2-Fluoroterephthalic Acid 4-methyl Ester (5)

A solution of 80% $NaClO_2$ (0.13 mol) in $H_2O$ (50 mL) is added dropwise to a solution of crude 3-fluoro-4-formyl benzoic acid methyl ester (4, 0.12 mol) and sulfamic acid (0.13 mol) in $H_2O$ (50 mL) and $CH_3CN$ (100 mL). After stirring for 1 h, the reaction mixture is poured into saturated $Na_2SO_3$ aqueous solution and 1 N HCl, and extracted three times with EtOAc. The combined organic layers are washed with brine, dried over $MgSO_4$, and evaporated in vacuo. The crystals are collected by filtration and washed with ether/hexane (1:1) to give 2-fluoroterephthalic acid 4-methyl ester (5) as white solid.

3-Fluoro-4-formyl Benzoic Acid Benzyl Ester (6)

60% NaH (0.23 mol) is added portionwise to a solution of 3-fluoro-4-formyl benzoic acid (3, 0.19 mol) in dry dimethylformamide (DMF) (570 mL). The mixture is stirred at room temperature for 45 min. Benzyl bromide (0.23 mol) is added dropwise to the mixture. After stirring at room temperature for 5 h, the reaction mixture is poured into 1N HCl (ca. 1000 mL) and extracted twice with EtOAc. The combined extracts are washed with saturated aqueous $NaHCO_3$, brine, dried over $MgSO_4$, and evaporated in vacuo to give crude 3-fluoro-4-formyl benzoic acid benzyl ester (6).

2-Fluoroterephthalic Acid 4-benzyl Ester (7)

A solution of 80% $NaClO_2$ (0.19 mol) in $H_2O$ (100 mL) is added dropwise to a solution of crude 3-fluoro-4-formyl benzoic acid benzyl ester (6, 0.19 mol) and sulfamic acid (0.19 mol) in $H_2O$ (300 mL) and $CH_3CN$ (150 mL). After stirring for 1 h, the reaction mixture is poured into 1 N HCl and extracted three times with EtOAc. The combined organic layers are washed with brine, dried over $MgSO_4$, and evaporated in vacuo. Crystals are collected by filtration and washed with ether/hexane (1:1) to give 2-fluoroterephthalic acid 4-benzyl ester (7) as white solid.

2-Fluoroterephthalic Acid 4-benzyl Ester 1-methyl Ester (8)

A solution of 2-fluoroterephthalic acid 4-benzyl ester (7) (0.14 mol) in $SOCl_2$ (60 mL) is stirred at 80° C. for 1 h. The mixture is cooled to room temperature and concentrated in vacuo to give a crude 4-chlorocarbonyl-2-fluorobenzoic acid benzylester. A solution of the crude in toluene (30 mL) is added dropwise to a solution of triethylamine (0.27 mol) in methanol (MeOH) (200 mL) over 10 min. After stirring for 1 h, the mixture is poured into 1 N HCl and extracted twice with EtOAc. The combined organic layers are washed with brine, dried over $MgSO_4$, and evaporated in vacuo to give crude 2-fluoroterephthalic acid 4-benzyl ester 1-methyl ester (8).

2-Fluoroterephthalic Acid 1-methyl Ester (9)

A solution of the crude 2-fluoroterephthalic acid 4-benzyl ester 1-methyl ester (8, 0.14 mol) in EtOH (210 mL) and EtOAc (210 mL) is treated with 10% Pd/C (4.0 g) under hydrogen atmosphere at room temperature for 5 h. After filtration of the catalyst, the filtrate is evaporated in vacuo. Crystals are collected and washed with ether/hexane (1:1) to give 2-fluoroterephthalic acid 1-methyl ester (9) as white solid.

Alternatively, 2-fluoroterephthalic acid 1-methyl ester (9) may be synthesized from 10 following the procedures from 1 to 5.

The benzodiazepine-derivatives of the present invention may for example be synthesized as described in the following paragraphs. In addition, a synthesis of the comparative examples as known in the prior art is described as well.

Synthesis of a Compound, for Example, of Formula (IIc), wherein $R_3$ is CO—$R_5$:

(2-Nitrophenyl)(5,5,8,8-tetramethyl-5,6,7,8-tetrahydronaphtalen-2-yl)amine

The compounds of the present invention may be obtained by the synthetic procedure described in EP 906'907, which is incorporated herein by reference. The starting material (11) may, for example, be synthesized according to the procedures reported by Ebisawa et al (Chem. Pharm. Bull., 1999, 47(12), 1778-1786).

Reaction scheme 2:
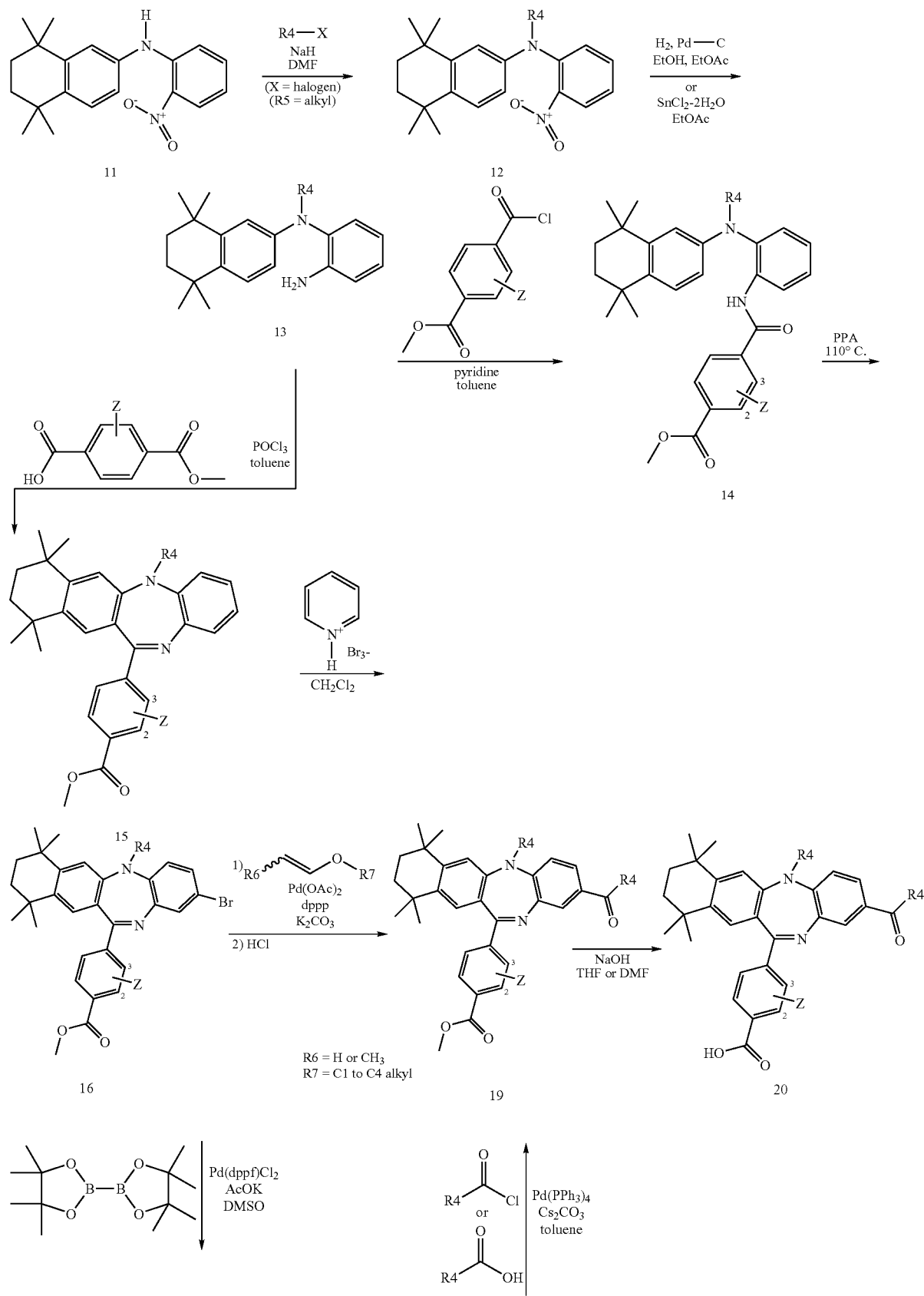

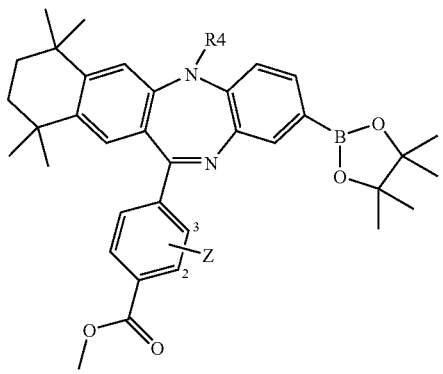

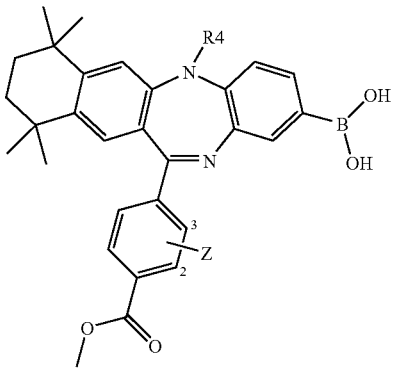

Methyl(2-nitrophenyl)(5,5,8,8-tetramethyl-5,6,7,8-tetrahydronaphtalen-2-yl)amine ($R_4=CH_3$) (12)

60% NaH (0.41 mol) is added portionwise to a solution of (2-nitrophenyl)(5,5,8,8-tetramethyl-5,6,7,8-tetrahydronaphtalen-2-yl)amine (11, 0.27 mol) in dry DMF (1770 mL) at 0° C. and stirred at room temperature for 45 min. To the mixture, methyl iodide (MeI) (30.6 mol) is added dropwise and the mixture is stirred at room temperature for 3 h. The reaction mixture is poured into ice water (ca. 2500 mL) and extracted with diethylether ($Et_2O$) (5×400 mL). The combined organic layer are washed with $H_2O$ (2×400 mL), dried over $MgSO_4$, and treated with $SiO_2$ (150 g). After evaporation of the solvent, the residue is loaded on a silica gel column. Flash column chromatography (2000 g Of $SiO_2$; hexane/EtOAc=10:1) gives the title compound (12) ($R_4=CH_3$).

N-Methyl-N-(5,5,8,8-tetramethyl-5,6,7,8-tetrahydronaphthalen-2-yl)-1,2-phenylene-diamine ($R_4=CH_3$) (13)

A solution of methyl(2-nitrophenyl)(5,5,8,8-tetramethyl-5,6,7,8-tetrahydronaphtalen-2-yl)amine (12) ($R_4=CH_3$, 0.26 mol) in EtOH (3200 mL) is treated with 10% Pd/C (8.9 g) under hydrogen atmosphere at room temperature for 2.5 h. After filtration of the catalyst, the filtrate is evaporated to give the above diamine (13) ($R_4=CH_3$).

N-{2-[Methyl(5,5,8,8-tetramethyl-5,6,7,8-tetrahydronaphthalen-2-yl)amino]-phenyl}-terephthalamic Acid Methyl Ester ($R_4=CH_3$, Z=H) (14)

A solution of oxalyl chloride (0.41 mol) in dry $CH_2Cl_2$ (1800 mL) is added dropwise over 15 min to a suspension of mono-methyl terephthalate (0.41 mol) and pyridine (0.45 mol) in dry $CH_2Cl_2$ (4400 mL) at room temperature. After stirring for 50 min at the same temperature, the mixture is evaporated and dried in vacuo. The resulting white powder is added to a solution of N-methyl-N-(5,5,8,8-tetramethyl-5,6,7,8-tetrahydronaphthalen-2-yl)-1,2-phenylenediamine (13) ($R_4=CH_3$, 0.27 mol) in dry pyridine (330 mL) and dry toluene (1200 mL) at room temperature. After stirring for 20 h, the mixture is cooled to 0° C., treated with 2 N HCl (2400 mL) and filtered. The layers of the filtrate are separated, and the aqueous layer is extracted with EtOAc (2×600 mL). The combined organic layers are washed with saturated aqueous $NaHCO_3$ (600 mL) and brine (600 mL), and dried over $MgSO_4$. The solution is treated with $SiO_2$ (180 g) and evaporated. The residue is loaded on a silica gel column. Flash column chromatography (2000 g of $SiO_2$; hexane/EtOAc=5:1) gives the ester (14) ($R_4=CH_3$, Z=H).

4-(5,7,7,10,10-Pentamethyl-7,8,9,10-tetrahydro-5H-5,13-diazabenzo[4,5]cyclohepta[1,2-b]naphthalen-12-yl)benzoic Acid Methyl Ester ($R_4=CH_3$, Z=H) (15)

A solution of N-{2-[methyl(5,5,8,8-tetramethyl-5,6,7,8-tetrahydronaphthalen-2-yl)amino]phenyl}terephthalamic acid methyl ester (14) ($R_4=CH_3$, Z=H, ~0.23 mol) in dry $CH_2Cl_2$ (108 mL) is treated with polyphosphoric acid (980 g) at room temperature and the temperature is slowly elevated from room temperature to 110° C. over 50 min with removing $CH_2Cl_2$ by distillation. After stirring for 24 h at 110° C., the mixture is cooled to 0° C., treated with $H_2O$ (3000 mL) and extracted with EtOAc (4×800 mL). The combined organic layers are washed with brine (800 mL), dried over $MgSO_4$, treated with $SiO_2$ (140 g), and evaporated. The residue is loaded on a silica gel column. Flash column chromatography (1600 g of $SiO_2$; hexane/EtOAc=4:1) gives the ester (15) ($R_4=CH_3$, Z=H) as yellow solid.

4-(5,7,7,10,10-Pentamethyl-7,8,9,10-tetrahydro-5H-5,13-diazabenzo[4,5]cyclohepta[1,2-b]naphthalen-12-yl)benzoic Acid Methyl Ester ($R_4=CH_3$, Z=H) (15)

A solution of N-methyl-N-(5,5,8,8-tetramethyl-5,6,7,8-tetrahydronaphthalen-2-yl)-1,2-phenylenediamine (13) (0.48 mol), terephthalic acid monomethyl ester (0.48 mol), and $POCl_3$ (0.95 mol) in dry toluene (1750 mL) is heated at 80° C. for 4 days. After cooling to room temperature, the mixture is diluted with EtOAc (1500 mL). The mixture is washed with 5 N NaOH, brine, dried over $MgSO_4$ and evaporated in vacuo. The residue is suspended in hexane. The crystals are collected by filtration and washed with hexane to give the ester (15) ($R_4=CH_3$, Z=H) as yellow solid.

4-(2-Bromo-5,7,7,10,10-pentamethyl-7,8,9,10-tetrahydro-5H-5,13-diazabenzo[4,5]-cyclohepta[1,2-b]naphthalen-12-yl)benzoic Acid Methyl Ester ($R_4=CH_3$, Z=H) (16)

A solution of 4-(5,7,7,10,10-pentamethyl-7,8,9,10-tetrahydro-5H-5,13-diazabenzo[4,5]-cyclohepta[1,2-b]naphthalen-12-yl)benzoic acid methyl ester (15) ($R_4=CH_3$, Z=H, 5.78 mmol) in $CH_2Cl_2$ (60 mL) is treated with pyridium tribromide (6.36 mmol) under nitrogen atmosphere at room temperature overnight. The reaction mixture is poured into aqueous $Na_2SO_3$ and extracted with $CH_2Cl_2$. The organic layer is washed twice with 10% $Na_2SO_3$, $H_2O$ and brine and dried over $MgSO_4$. After evaporation of the solvent, the residue is purified by flash column chromatography (SiO$_2$; hexane/EtOAc=20:1) to give bromide (16) (R$_4$=CH$_3$, Z=H).

4-(2-Acetyl-5,7,7,10,10-pentamethyl-7,8,9,10-tetrahydro-5H-5,13-diazabenzo[4,5]-cyclohepta[1,2-b]naphthalen-12-yl)benzoic Acid Methyl Ester (R$_4$=CH$_3$, Z=H, R$_5$=CH$_3$) (19)

A mixture of 4-(2-bromo-5,7,7,10,10-pentamethyl-7,8,9,10-tetrahydro-5H-5,13-diazabenzo[4,5]cyclohepta[1,2-b]naphthalen-12-yl)benzoic acid methyl ester (16, R$_5$=CH$_3$, Z=H, 1.9 mmol), butyl vinyl ether (4.8 mmol), Pd(OAc)$_2$ (0.058 mmol), DPPP (0.11 mmol), K$_2$CO$_3$ (2.3 mmol), and H$_2$O (0.3 mL) in DMF (5 mL) is stirred at 120° C. for 1.5 h under nitrogen atmosphere. After cooling to room temperature, the mixture is poured into 1N HCl and extracted twice with EtOAc. The combined extracts are washed with H$_2$O, brine, dried over MgSO$_4$ and evaporated in vacuo. The residue is purified by flash column chromatography (SiO$_2$; hexane: EtOAc=9:1 to 3:1) to give the ester (19) (R$_4$=CH$_3$, Z=H, R$_5$=CH$_3$) as yellow solid.

4-[5,7,7,10,10-Pentamethyl-2-(4,4,5,5-tetramethyl-[1,3,2]dioxaborolan-2-yl)-7,8,9,10-tetrahydro-5H-5,13-diazabenzo[4,5]cyclohepta[1,2-b]naphthalen-12-yl]benzoic Acid Methyl Ester (R$_4$=CH$_3$, Z=H) (17)

A mixture of 4-(2-bromo-5,7,7,10,10-pentamethyl-7,8,9,10-tetrahydro-5H-5,13-diazabenzo[4,5]cyclohepta[1,2-b]naphthalen-12-yl)benzoic acid methyl ester (16) (R$_4$=CH$_3$, Z=H, 4.8 mmol), bis(pinacolato)diboron (5.8 mmol), Pd(dppf)Cl$_2$ (0.15 mmol) and KOAc (14 mmol) in dimethyl sulfoxide (DMSO) (20 mL) is stirred at 90° C. for 3.5 h under nitrogen atmosphere. After cooling to room temperature, the mixture is poured into 1 N HCl and extracted twice with EtOAc. The combined organic layers are washed with brine, dried over MgSO$_4$ and evaporated in vacuo. The residue is purified by flash column chromatography (SiO$_2$; hexane: EtOAc=8:1 to 4:1) to give the ester (17) (R$_4$=CH$_3$, Z=H) as yellow solid.

4-[2-(4-Chlorobenzoyl)-5,7,7,10,10-pentamethyl-7,8,9,10-tetrahydro-5H-5,13-diazabenzo[4,5]cyclohepta[1,2-b]naphthalen-12-yl]benzoic Acid Methyl Ester (R$_4$=CH$_3$, Z=H, R$_5$=4-chlorophenyl) (19)

A solution of 4-[5,7,7,10,10-pentamethyl-2-(4,4,5,5-tetramethyl-[1,3,2]dioxa-borolan-2-yl)-7,8,9,10-tetrahydro-5H-5,13diazabenzo[4,5]cyclohepta[1,2-b]naphthalen-12-yl] benzoic acid methyl ester (17) (R5=CH$_3$, Z=H, 0.89 mmol) and phenyl boronic acid (1.8 mmol) in THF(=tetrahydrofuran)/MeOH (4:3, 14 mL) is treated with 2 N HCl (14 mL). After stirring for 5 h, the mixture is extracted with EtOAc. The extract is washed with brine, dried over MgSO$_4$ and evaporated in vacuo. The resulting residue is purified by flash column chromatography (SiO$_2$; hexane: EtOAc 4:1 to 1:1) to give 12-(4-methoxycarbonylphenyl)-5,7,7,10,10-pentamethyl-7,8,9,10-tetrahydro-5H-5,13-diazabenzo[4,5]cyclohepta[1,2-b]naphthalene-2-boronic acid (18) (R$_4$=CH$_3$, Z=H) contaminated with phenyl boronic acid.

A mixture of the above boronic acids, 4-chlorobenzoylchloride (1.6 mmol), Pd(PPh$_3$)$_4$ (0.040 mmol) and Cs$_2$CO$_3$ (2.0 mmol) in toluene (20 mL) is stirred at 90° C. for 9 h under nitrogen atmosphere. After cooling to room temperature, the mixture is poured into 1 N HCl and extracted twice with EtOAc. The combined organic layers are washed with, brine, dried over MgSO$_4$ and evaporated in vacuo. The residue is purified by flash column chromatography (SiO$_2$; hexane: EtOAc=7:1) to give the ester (19) (R$_4$=CH$_3$, Z=H, R$_5$=4-chlorophenyl) as yellow solid.

4-(2-Acetyl-5,7,7,10,10-pentamethyl-7,8,9,10-tetrahydro-5H-5,13-diazabenzo[4,5-]cyclohepta[1,2-b]naphthalen-12-yl)benzoic acid (R$_4$=CH$_3$, Z=H, R$_5$=CH$_3$) (20)

A solution of 4-[5,7,7,10,10-pentamethyl-2-(4,4,5,5-tetramethyl-[1,3,2]dioxa-borolan-2-yl)-7,8,9,10-tetrahydro-5H-5,13diazabenzo[4,5]cyclohepta[1,2-b]naphthalen-12-yl] benzoic acid methyl ester (19) (R$_4$=CH$_3$, Z=H, R$_5$=CH$_3$, 0.90 mmol) in THF/MeOH (3:1, 4 mL) is treated with 1 N NaOH (1 mL) and the mixture is stirred for 12 h. The mixture is poured into 1 N HCl and extracted with EtOAc. The extract is washed with brine, dried over MgSO$_4$ and evaporated in vacuo. The resulting solids are collected by filtration and washed with ether/hexane (1:10) to give the benzoic acid (20) (R$_4$=CH$_3$, Z=H, R$_5$=CH$_3$) as yellow solid:
$^1$H-NMR (CDCl$_3$) δ: 1.06 (3H, t), 1.14 (3H, s), 1.27 (3H, s), 1.32 (3H, s), 1.61-1.70 (4H, m), 2.59 (3H, s), 3.30 (3H, s), 6.89 (1H, s), 6.93 (1H, s), 7.01 (1H, d), 7.79 (1H, dd), 7.89 (1H, d), 7.93 (2H, d), 8.16 (2H, d); $^1$H-NMR (DMSO-d$_6$) δ: 0.91 (3H, t), 1.01 (3H, s), 1.15 (3H, s), 1.19 (3H, s), 1.45-1.55 (4H, m), 2.44 (3H, s), 3.16 (3H, s), 6.77 (1H, s), 6.98 (1H, s), 7.07 (1H, d), 7.63-7.69 (2H, m), 7.72 (1H, d), 7.93 (2H, d), 13.03 (1H, br).

Reaction scheme 3:

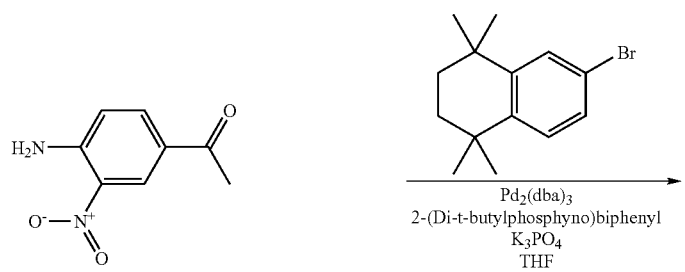

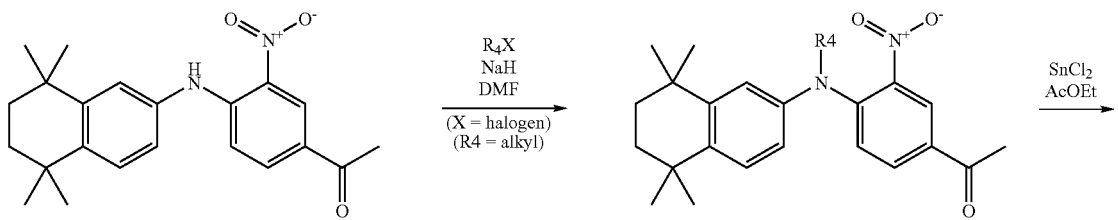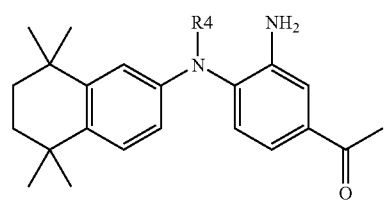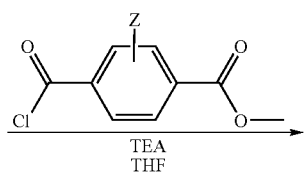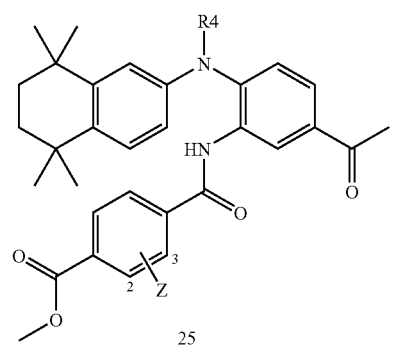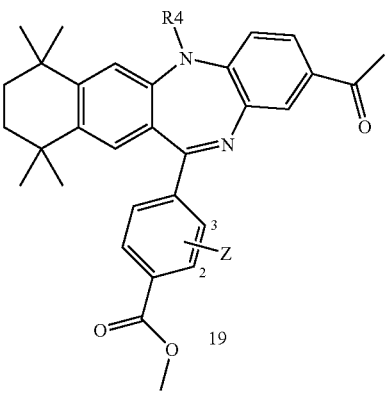

4-Amino-3-nitroacetophenone (21) is synthesized according to the procedures reported by Thomas C. Kuhler et al (Journal of Medicinal Chemistry., 1998, 41(11), 1777-1788) or WO96/33191.

3-Nitro-4-(5,5,8,8-tetramethyl-5,6,7,8-tetrahydronaphthalen-2-ylamino)acetophenone (22)

To a solution of 6-bromo-1,1,4,4-tetramethyl-1,2,3,4-tetrahydronaphthalene (48 mmol) and 4-amino-3-nitroacetophenone (21) (44 mmol) in THF (130 mL) are added $K_3PO_4$-$nH_2O$ (65 mmol), 2-(di-t-butylphosphino)biphenyl (2.2 mmol), and $Pd_2(bda)_3$ (1.1 mmol) at room temperature. The reaction mixture is heated at 70° C. for 17 h. After cooling, the mixture is filtered through Celite. The filtrate is diluted with $H_2O$ and extracted with EtOAc. The organic layer is washed with 1 N HCl, brine, dried over $MgSO_4$ and evaporated in vacuo. The resulting solid is washed with $Et_2O$ to give the acetophenone (22).

4-[Methyl(5,5,8,8-tetramethyl-5,6,7,8-tetrahydronaphthalen-2-yl)amino]-3-nitroacetophenone ($R_4$=$CH_3$) (23)

60% NaH (11 mmol) is added portionwise to a solution of 3-nitro-4-(5,5,8,8-tetramethyl-5,6,7,8-tetrahydronaphthalen-2-ylamino)acetophenone (22, 11 mmol) in dry DMF (36 mL) and stirred at room temperature for 45 min. To the mixture, MeI (12 mmol) is added dropwise and the mixture is stirred at room temperature for 14 h. The reaction mixture is poured into ice water and extracted twice with EtOAc. The combined organic layers are washed with $H_2O$, brine, dried over $MgSO_4$, and treated with $SiO_2$ (12 g). After evaporation of the solvent, the residue is loaded on a silica gel column. Flash column chromatography (200 g of $SiO_2$; hexane/EtOAc=10:1) gives the acetophenone (23) ($R_4$=$CH_3$).

3-Amino-4-[methyl(5,5,8,8-tetramethyl-5,6,7,8-tetrahydronaphthalen-2-yl)aminoacetophenone ($R_4$=$CH_3$) (24)

$SnCl_2$-$2H_2O$ (21 mmol) is added to a solution of 4-[methyl-(5,5,8,8-tetramethyl-5,6,7,8-tetrahydronaphthalen-2-yl)amino]-3-nitroacetophenone (23) ($R_4$=$CH_3$, 4.3 mmol) in EtOAc (30 mL) and the mixture is heated at 80° C. for 1 h. After cooling, to the reaction mixture are successively added crash-ice and 1N NaOH (55 mL). The reaction mixture is filtered through Celite (9 g) and washed with EtOAc. The organic layer is washed with saturated aqueous $NaHCO_3$, brine, dried over $MgSO_4$ and evaporated in vacuo. The resulting solid is washed with hexane to give the amine (24) ($R_4$=$CH_3$).

N-{5-Acetyl-2-[methyl(5,5,8,8tetramethyl-5,6,7,8-tetrahydronaphthalen-2-yl)amino]phenyl}-3-fluoroterephthalamic Acid Methyl Ester ($R_4$=$CH_3$, Z=3-F) (25)

Oxalyl chloride (6.7 mmol) is added dropwise to a solution of 2-fluoroterephthalic acid 4-methyl ester (6.2 mmol), and 1 drop of DMF in dry $CH_2Cl_2$ (30 mL) at room temperature. After stirring for 2 h, the mixture is concentrated in vacuo. The resulting residue in THF (15 mL) is added dropwise to a solution of 3-amino-4-[methyl(5,5,8,8-tetramethyl-5,6,7,8-tetrahydronaphthalen-2-yl)aminoacetophenone (24) $R_4$=$CH_3$, 5.6 mmol), dry triethylamine (7.3 mmol) in dry THF (35 mL) at room temperature. After stirring for 2 h, the mixture is treated with water and extracted three times with EtOAc. The combined organic layers are washed with saturated aqueous $NaHCO_3$, brine, and dried over $MgSO_4$. The solution is evaporated in vacuo and the residue is purified by flash column chromatography (100 g of $SiO_2$; hexane/EtOAc=10:1 to 4:1) to give the ester (25) ($R_4$=$CH_3$, Z=3-F).

4-(2-Acetyl-5,7,7,10,10-pentamethyl-7,8,9,10-tetrahydro-5H-5,13-diazabenzo[4,5]cyclohepta[1,2-b]naphthalen-12-yl)-3-fluorobenzoic Acid Methyl Ester ($R_4$=$CH_3$, Z=3-F) (19)

A solution of N-{5-acetyl-2-[methyl(5,5,8,8-tetramethyl-5,6,7,8-tetrahydronaphthalen-2-yl)amino]phenyl}-3-fluoroterephthalamic acid methyl ester (25) ($R_4$=$CH_3$, Z=3-F, 0.57 mmol) in dry $CH_2Cl_2$ (0.5 mL) is treated with polyphosphoric acid (5 g) at room temperature and the temperature is slowly elevated from room temperature to 120° C. After stirring at 120° C. for 1 h, the mixture is cooled to room temperature, poured into crash-ice, and extracted twice with EtOAc. The combined organic layers are washed with saturated aqueous $NaHCO_3$, brine, and dried over $MgSO_4$. The extract is treated with $SiO_2$ (1.5 g), and evaporated. The residue is loaded on a silica gel column. Flash column chromatography (15 g of $SiO_2$; hexane/EtOAc=10:1 to 2:1) gives the ester ($R_4$=$CH_3$, Z=3-F) (19).

4-(2-Acetyl-5,7,7,10,10-pentamethyl-7,8,9,10-tetrahydro-5H-5,13-diazabenzo[4,5]cyclohepta[1,2-b]naphthalen-12-yl)-3-fluorobenzoic Acid ($R_4$=$CH_3$, Z=3-F) (20)

A solution of 4-(2-acetyl-5,7,7,10,10-pentamethyl-7,8,9,10-tetrahydro-5H-5,13-diazabenzo[4,5]cyclohepta[1,2-b]naphthalen-12-yl)-3-fluorobenzoic acid methyl ester (19) ($R_4$=$CH_3$, Z=3-F, 0.25 mmol) in the mixture of THF (2.5 mL) and MeOH (0.14 mL) is treated with 1N NaOH (0.41 mL) and the mixture is stirred for 12 h. The mixture is poured into 1N HCl and extracted with EtOAc. The extract is washed with brine, dried over $MgSO_4$ and evaporated in vacuo. The resulting solids are collected by filtration and washed with $Et_2O$ to give the acid (20) ($R_4$=$CH_3$, Z=3-F) as yellow solid: $^1$H-NMR (DMSO-$d_6$) δ: 1.00 (6H, s), 1.26 (6H, s), 1.53-1.62 (4H, m), 2.55 (3H, s), 3.29 (3H, s), 6.75 (1H, s), 7.03 (1H, s), 7.18 (1H, d), 7.71 (1H, d), 7.75 (1H, d), 7.81 (1H, dd), 7.90-7.98 (2H, m), 13.47 (1H, br).

In similar procedures described above, the following analogs are prepared.

4-(2-Acetyl-5,7,7,10,10-pentamethyl-7,8,9,10-tetrahydro-5H-5,13-diazabenzo[4,5]cyclohepta[1,2-b]naphthalen-12-yl)-2-fluorobenzoic Acid ($R_4$=$CH_3$, Z=2-F) (20a)

$^1$H-NMR (DMSO-$d_6$) δ: 1.04 (3H, s), 1.14 (3H, s), 1.25 (3H, s), 1.30 (3H, s), 1.56-1.65 (4H, m), 2.55 (3H, s), 3.27 (3H, s), 6.94 (1H, s), 7.10 (1H, s), 7.17 (1H, d), 7.54 (1H, dd), 7.66 (1H, dd), 7.78 (1H, dd), 7.81 (1H, d), 7.96 (1H, dd), 13.46 (1H, br).

4-(2-Acetyl-5-ethyl-7,7,10,10-tetamethyl-7,8,9,10-tetrahydro-5H-5,13-diazabenzo[4,5]cyclohepta[1,2-b]naphthalen-12-yl)benzoic Acid, ($R_4$=$C_2H_5$, Z=H) (20b)

$^1$H-NMR (DMSO-$d_6$) δ: 1.13 (3H, s), 1.24 (3H, s), 1.26 (3H, t), 1.36 (3H, s), 1.41 (3H, s), 1.66-1.76 (4H, m), 2.66 (3H, s), 3.77-3.84 (2H, m), 3.90-3.98 (1H, m), 7.02 (1H, s), 7.18 (1H, s), 7.29 (1H, d), 7.86-7.90 (2H, m), 7.96 (2H, d), 8.16 (2H, d), 13.19 (1H, br).

4-(2-Acetyl-5-ethyl-7,7,10,10-tetramethyl-7,8,9,10-tetrahydro-5H-5,13-diazabenzo[4,5]-cyclohepta[1,2-b]naphthalen-12-yl)-3-fluorobenzoic Acid
($R_4=C_2H_5$, Z=3-F) (20c)

$^1$H-NMR (DMSO-$d_6$) δ: 1.01 (6H, s), 1.18 (3H, t), 1.23 (3H, s), 1.28 (3H, s), 1.55-1.62 (4H, m), 2.55 (3H, s), 3.64-3.75 (2H, m), 3.86-3.94 (1H, m), 6.78 (1H, s), 7.02 (1H, s), 7.19 (1H, d), 7.72 (1H, d), 7.77 (1H, d), 7.82 (1H, dd), 7.90-7.97 (2H, m), 13.39 (1H, br).

By repeating the procedures described above using appropriate starting materials and conditions, the following compounds are obtained.

| Example | Structure | Rf value (solvent) | MS ($M^+ + 1$) |
|---------|-----------|--------------------|-----------------|
| 20d | 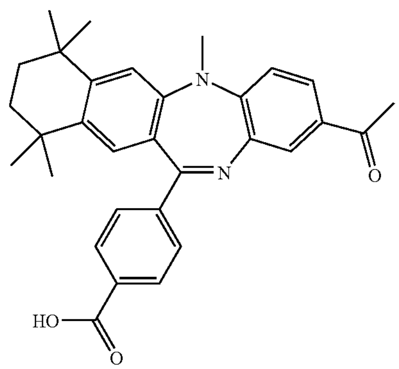 | 0.22 (CHCl$_3$:MeOH = 9:1) | 481 |
| 20e | 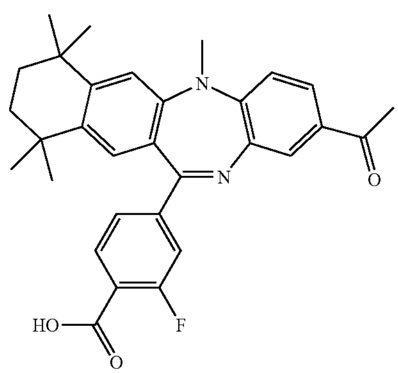 | 0.20 (CHCl$_3$:MeOH = 10:1) | 499 |
| 20f | 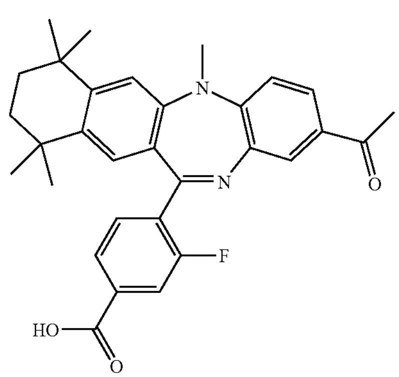 | 0.23 (CHCl$_3$:MeOH = 10:1) | 499 |

-continued

| Example | Structure | Rf value (solvent) | MS (M⁺ + 1) |
|---------|-----------|--------------------|--------------|
| 20g | 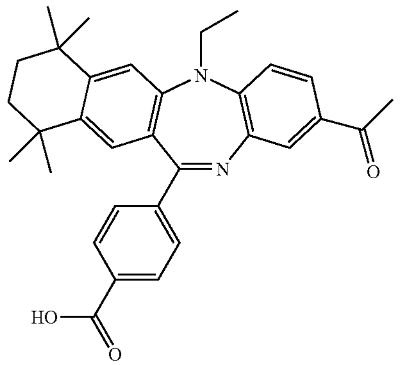 | 0.23 (CHCl₃:MeOH = 9:1) | 495 |
| 20h | 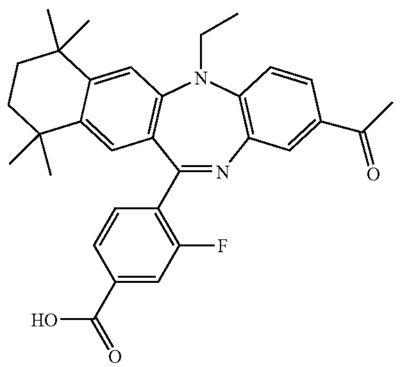 | 0.19 (CHCl₃:MeOH = 9:1) | 513 |
| 20i | 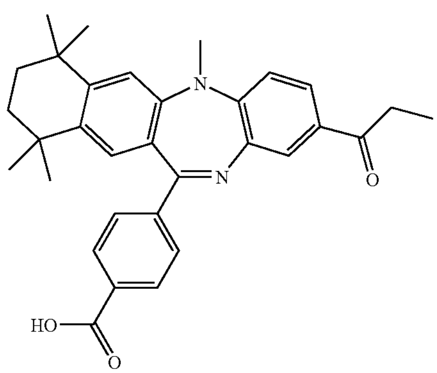 | 0.28 (CHCl₃:MeOH = 9:1) | 495 |
| 20j | 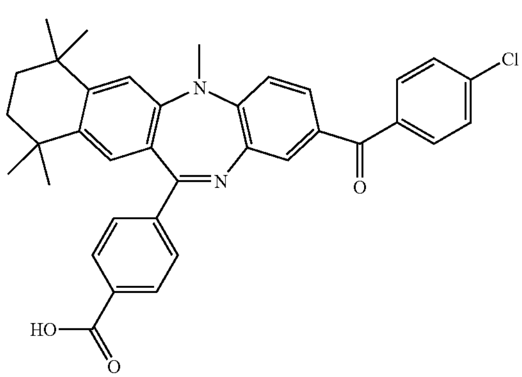 | 0.33 (CHCl₃:MeOH = 9:1) | 577 |

Synthesis of a Compound, for Example, of Formula (IIc), wherein $R_3$ Hydrogen and $R_4$ is $C_3$-$C_7$-alkenyl, or $C_3$-$C_7$-alkynyl, or $C_2$-$C_7$-alkanoyl:

Reaction scheme 4:

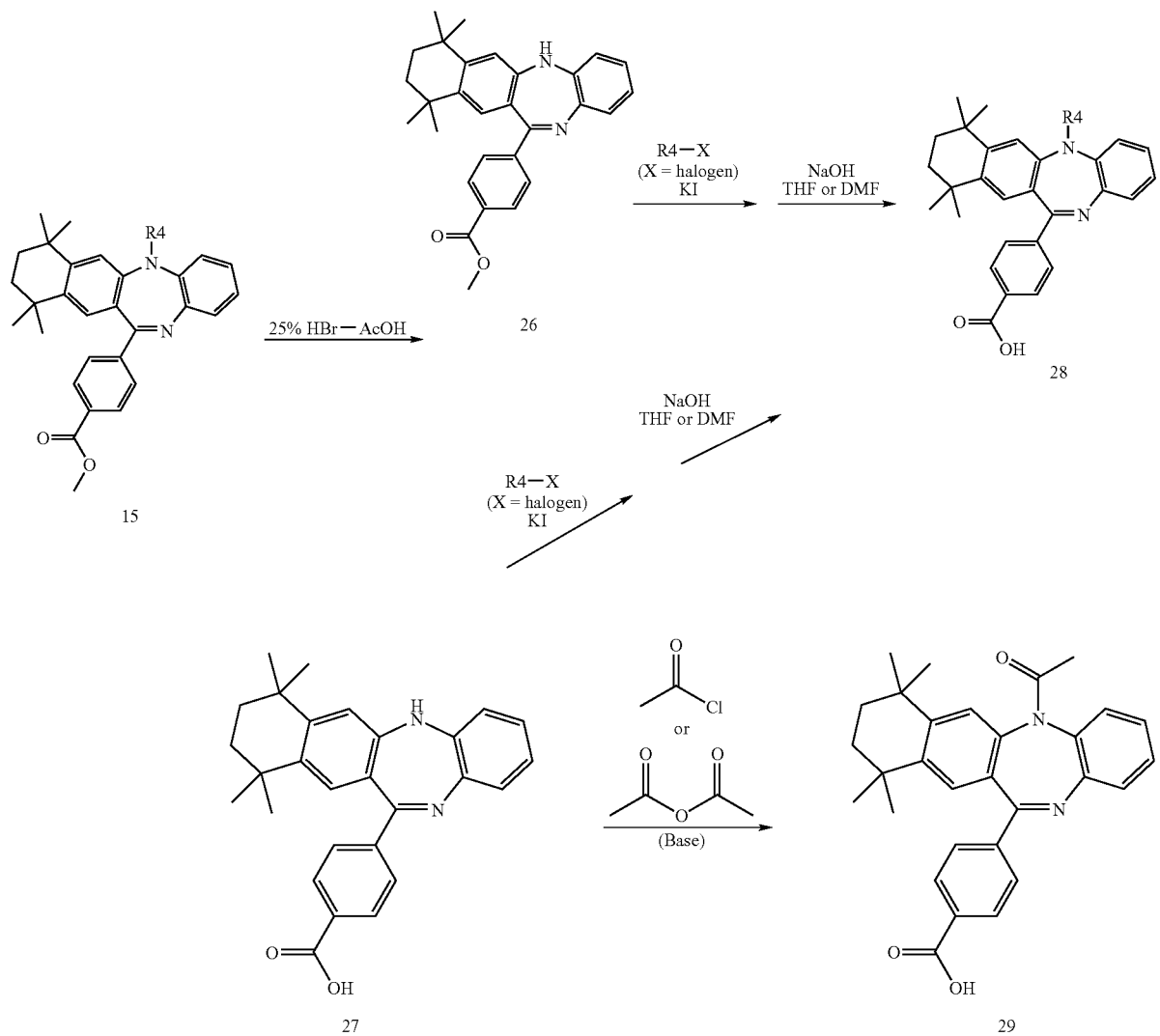

4-(7,7,10,10-Pentamethyl-7,8,9,10-tetrahydro-5H-5, 13-diazabenzo[4,5]cyclohepta[1,2-b]naphthalen-12-yl)benzoic Acid Methyl Ester (26); and 4-(7,7,10,10-Tetramethyl-7,8,9,10-tetrahydro-5H-5, 13-diazabenzo[4,5]cyclohepta[1,2-b]naphthalen-12-yl)benzoic Acid (27)

A solution of 4-(7,7,10,10-tetramethyl-5-propyl-7,8,9,10-tetrahydro-5H-5,13-diazabenzo[4,5]cyclohepta[1,2-b]naphthalen-12-yl)benzoic acid methyl ester (15) ($R_4$=$C_3H_7$, 10 mmol) in 25% HBr-AcOH (35 mL) is heated at 90° C. for 17 h. After cooling to room temperature, the reaction mixture is poured into ice-water and extracted with EtOAc. The extract is washed with saturated aqueous $NaHCO_3$, brine, dried over $MgSO_4$, and evaporated in vacuo. The residue is purified by flash column chromatography ($SiO_2$; hexane/EtOAc=3:1 to 0:1) to give the ester (26) and the acid (27).

4-(5-Acetyl-7,7,10,10-tetramethyl-7,8,9,10-tetrahydro-5H-5,13-diazabenzo[4,5]-cyclohepta[1,2-b]naphthalen-12-yl)benzoic Acid ($R_8$=$CH_3$) (29)

A solution 4-(7,7,10,10-tetramethyl-7,8,9,10-tetrahydro-5H-5,13-diazabenzo[4,5]-cyclohepta[1,2-b]naphthalen-12-yl)benzoic acid (27) (0.47 mmol) and pyridine (1.2 mmol) in $CH_2Cl_2$ (4 mL) is treated with acetyl chloride (1.0 mmol) and stirred at room temperature for 6 h. The mixture is poured into 1 N HCl and extracted with EtOAc. The extract is washed with brine, dried over $MgSO_4$ and evaporated in vacuo. The resulting solid is purified by reversed-phase HPLC (0.1% TFA, 30-100% gradient CH$_3$CN) to give the acid (29).

4-(5-Allyl-7,7,10,10-tatramethyl-7,8,9,10-tetrahydro-5H-5,13-diazabenzo[4,5]-cyclohepta[1,2-b]naphthalen-12-yl)benzoic Acid (R$_4$=allyl) (28)

60% NaH (4.2 mmol) is added portionwise to a solution of 4-(7,7,10,10-tetramethyl-7,8,9,10-tetrahydro-5H-5,13-diazabenzo[4,5]cyclohepta[1,2-b]naphthalen-12-yl)benzoic acid (27) (1.9 mmol) in dry DMF (7 mL) and stirred at room temperature for 45 min. Allyl bromide (9.4 mmol) and KI (4.2 mmol) are added to the mixture. After stirring for 13 h, the reaction mixture is poured into ice-water and extracted with EtOAc. The extract is washed with brine, dried over MgSO$_4$, and evaporated in vacuo to give a crude 4-(5-allyl-7,7,10,10-tetramethyl-7,8,9,10-tetrahydro-5H-5,13-diazabenzo[4,5]cyclohepta[1,2-b]naphthalen-12-yl)benzoic acid allyl ester.

A solution of the above crude in DMF (10 mL) is treated with 2 N NaOH (2 mL) and the mixture is stirred for 16 h. The mixture is poured into 1 N HCl and extracted with EtOAc. The extract is washed with brine, dried over MgSO$_4$ and evaporated in vacuo. The resulting residue is purified by reversed-phase HPLC (0.1% TFA, 30-100% gradient CH$_3$CN) to give the acid (28) (R$_4$=allyl).

By repeating the procedures described above using appropriate starting materials and conditions, the following compounds are obtained.

Synthesis of a Compound, for Example, of Formula (IIc), wherein R$_3$ is Cyano:

Reaction scheme 5:

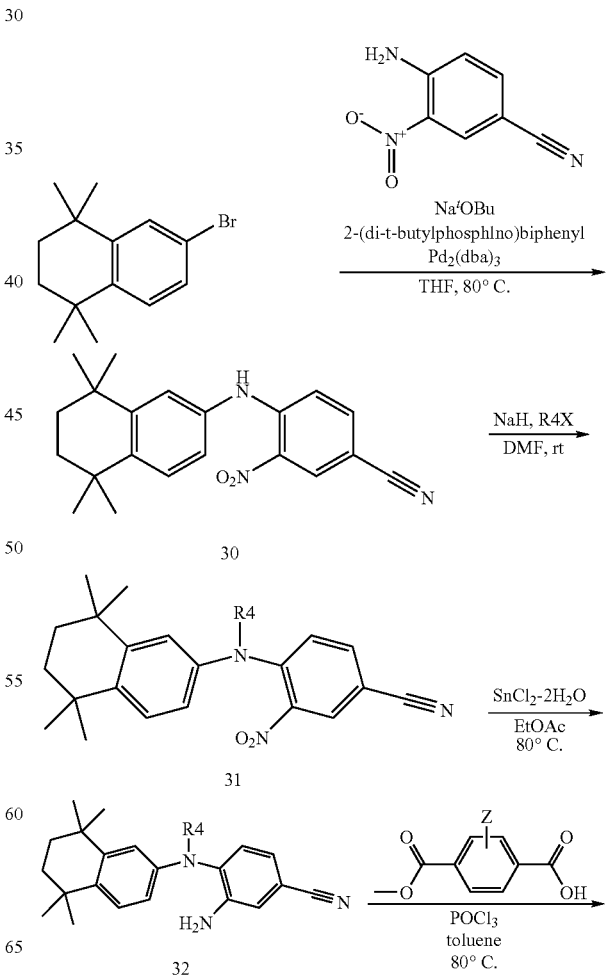

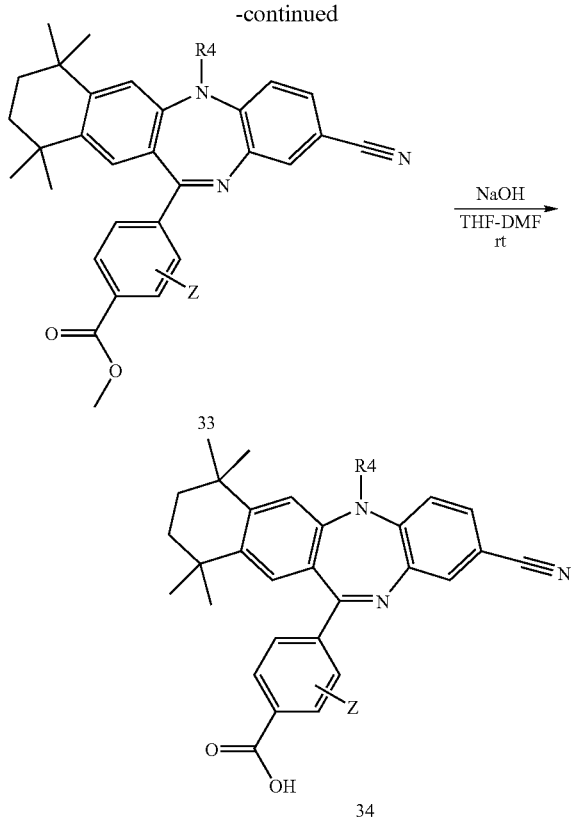

3-Nitro-4-(5,5,8,8-tetramethyl-5,6,7,8-tetrahydronaphthalen-2-ylamino)benzonitrile (30)

To a solution of 6-bromo-1,1,4,4-tetramethyl-1,2,3,4-tetrahydronaphthalene (61.3 mmol) and 4-amino-3-nitrobenzonitrile (61.3 mmol) in THF (150 mL) are added NaOtBu (67.4 mmol), 2-(t-butylphosphino)biphenyl (6.13 mmol), and $Pd_2(bda)_3$ (3.06 mmol) at room temperature. The reaction mixture is heated at 80° C. for 2 h. After cooling, the mixture is filtered through Celite. The filtrate is diluted with $H_2O$ and extracted with EtOAc. The organic layer is dried over $MgSO_4$ and evaporated in vacuo. The resulting solid is washed with a mixture of hexane and EtOAc (8:1) to give (30).

4-[Methyl-(5,5,8,8-tetramethyl-5,6,7,8-tetrahydronaphthalen-2-yl)amino]-3-nitrobenzonitrile ($R_4$=$CH_3$) (31)

NaH (60%, 6.44 mmol) is added portionwise to a solution of 3-nitro-4-(5,5,8,8-tetramethyl-5,6,7,8-tetrahydronaphthalen-2-ylamino)benzonitrile (30, $R_4$=$CH_3$, 4.29 mmol) in DMF (15 mL) at 0° C. The reaction mixture is slowly warmed up to room temperature and stirred for 1 h. To the mixture is added dropwise MeI (6.44 mmol) and the reaction mixture is stirred at room temperature for 5 h. The mixture is diluted with $H_2O$ and extracted with $Et_2O$. The organic layer is dried over $MgSO_4$ and evaporated in vacuo. The resulting solid is washed with hexane to give (31) ($R_4$=$CH_3$).

3-Amino-4-[methyl-(5,5,8,8-tetramethyl-5,6,7,8-tetrahydronaphthalen-2-yl)amino]benzonitrile ($R_4$=$CH_3$) (32)

$SnCl_2 \cdot 2H_2O$ (0.17 mol) is added to a solution of 4-[methyl-(5,5,8,8-tetramethyl-5,6,7,8-tetrahydronaphthalen-2-yl)amino]-3-nitrobenzonitrile (31) ($R_4$=$CH_3$, 34.0 mmol) in EtOAc (125 mL) and the mixture is heated at 80° C. for 1 h. After cooling, to the reaction mixture are successively added 6N NaOH (120 mL), $H_2O$ (150 mL), and EtOAc (150 mL). The reaction mixture is filtered through Celite (25 g) and washed with EtOAc. The organic layer is dried over $MgSO_4$ and evaporated in vacuo. The resulting solid is washed with hexane to give (32) ($R_4$=$CH_3$).

4-(2-Cyano-5,7,7,10,10-pentamethyl-7,8,9,10-tetrahydro-5H-5,13-diaza-benzo[4,5]-cyclohepta[1,2-b]naphthalen-12-yl)benzoic Acid Methyl Ester ($R_4$=$CH_3$, Z=H) (33)

A mixture of 3-amino-4-[methyl-(5,5,8,8-tetramethyl-5,6,7,8-tetrahydronaphthalen-2-yl)amino]benzonitrile (32) ($R_4$=$CH_3$, 30.0 mmol), terephthalic acid monomethyl ester (30.0 mmol), $POCl_3$ (69.0 mmol), and toluene (200 mL) is heated at 80° C. for 3 days. After cooling, the reaction mixture is treated with 1 N HCl (100 mL) and $H_2O$ (100 mL) and extracted with EtOAc. The organic layer is dried over $MgSO_4$ and evaporated in vacuo. The residue is purified by flash column chromatography (hexane:EtOAc=5:1) to give (33) ($R_4$=$CH_3$, Z=H).

4-(2-Cyano-5,7,7,10,10-pentamethyl-7,8,9,10-tetrahydro-5H-5,13-diazabenzo[4,5]-cyclohepta[1,2-b]naphthalen-12-yl)benzoic Acid ($R_4$=$CH_3$, Z=H) (34)

To a solution of 4-(2-cyano-5,7,7,10,10-pentamethyl-7,8,9,10-tetrahydro-5H-5,13-diazabenzo[4,5]cyclohepta[1,2-b]naphthalen-12-yl)benzoic acid methyl ester (33) ($R_4$=$CH_3$, Z=H, 12.3 mmol) in DMF (15 mL) and THF (45 mL) is added 2 N NaOH (18.5 mmol) at room temperature. The reaction mixture is stirred at the same temperature for 1 day. The mixture is acidified by 1 N HCl (30 mL), diluted with $H_2O$, and extracted with EtOAc. The organic layer is dried over $MgSO_4$ and evaporated in vacuo. The resulting solid is washed with hexane and $Et_2O$ to give (34) ($R_4$=$CH_3$, Z=H): $^1$H-NMR ($CDCl_3$) δ: 1.08 (3H, s), 1.15 (3H, s), 1.28 (3H, s), 1.32 (3H, s), 1.61-1.72 (4H, m), 3.28 (3H, s), 6.90 (1H, s), 6.63 (1H, s), 6.99 (1H, d), 7.41 (1H, dd), 7.57 (1H, d), 7.90 (2H, d), 8.17 (2H, d).

In the similar procedures described above, the following analogues are prepared.

4-(2-Cyano-5-ethyl-7,7,10,10-tetramethyl-7,8,9,10-tetrahydro-5H-5,13-diazabenzo[4,5]-cyclohepta[1,2-b]naphthalen-12-yl)benzoic Acid ($R_4$=$C_2H_5$, Z=H) (34a)

$^1$H-NMR ($CDCl_3$) δ: 1.07 (3H, s), 1.16 (3H, s), 1.26 (3H, t), 1.27 (3H, s), 1.31 (3H, s), 1.62-1.71 (4H, m), 3.59-3.82 (2H, m), 6.90 (1H, s), 6.92 (1H, s), 7.00 (1H, d), 7.42 (1H, dd), 7.59 (1H, d), 7.92 (2H, d), 8.18 (2H, d).

4-(2-Cyano-5,7,7,10,10-pentamethyl-7,8,9,10-tetrahydro-5H-5,13-diaza-benzo[4,5]-cyclohepta[1,2-b]naphthalen-12-yl)-2-fluoro-benzoic Acid ($R_4$=$CH_3$, Z=2-F) (34b)

$^1$H-NMR (DMSO-$d_6$) δ: 1.05 (3H, s), 1.13 (3H, s), 1.26 (3H, s), 1.29 (3H, s), 1.56-1.69 (4H, m), 3.26 (3H, s), 6.95 (2H, s), 7.09 (1H, s), 7.22 (1H, d), 7.50 (1H, dd), 7.63-7.68 (3H, d), 7.92 (1H, t), 13.47 (1H, br s).

4-(2-Cyano-5-ethyl-7,7,10,10-tetramethyl-7,8,9,10-tetrahydro-5H-5,13-diazabenzo[4,5]-cyclohepta[1,2-b]naphthalen-12-yl)-3-fluoro-benzoic Acid ($R_4=C_2H_5$, Z=3-F) (34c)

$^1$H-NMR (DMSO-$d_6$) δ: 1.08 (3H, s), 1.10 (3H, s), 1.24 (3H, t), 1.31 (3H, s), 1.35 (3H, s), 1.57-1.73 (4H, m), 3.68-3.79 (1H, m), 3.92-4.06 (1H, m), 6.87 (1H, s), 7.11 (1H, s), 7.32 (1H, d), 7.68-7.82 (3H, m), 7.99-8.04 (2H, m), 13.53 (1H, br s).

In the case of the N-allyl derivative (38), the compound may be obtained as shown in the following scheme using appropriate starting materials and conditions.

Reaction scheme 6:

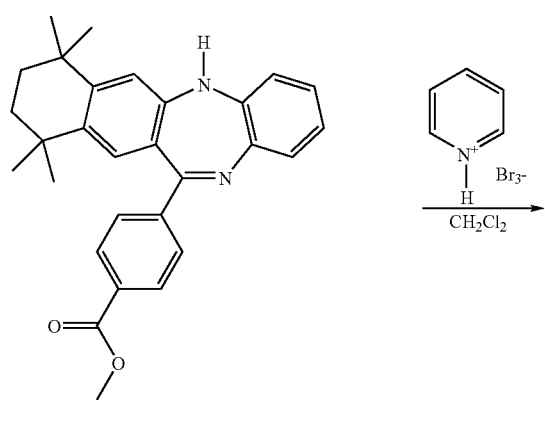

26

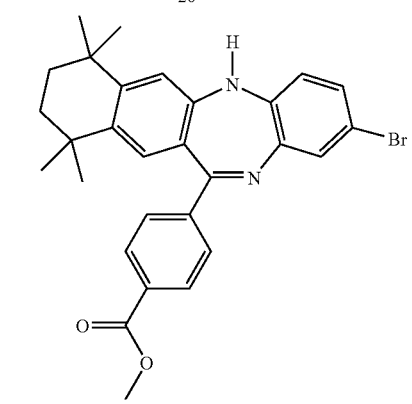

35

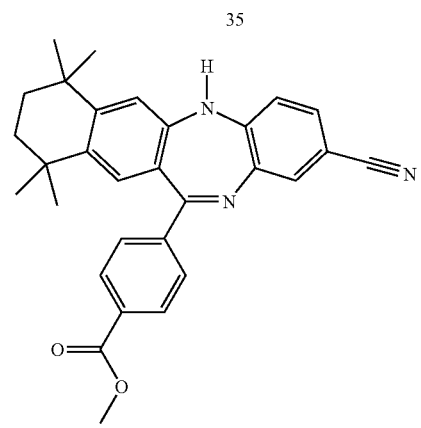

36

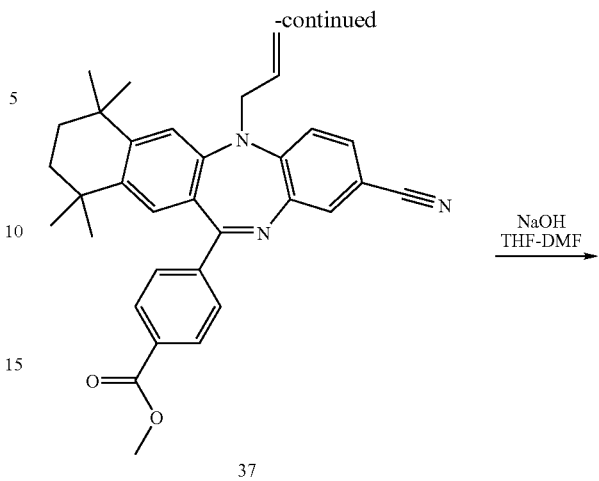

37

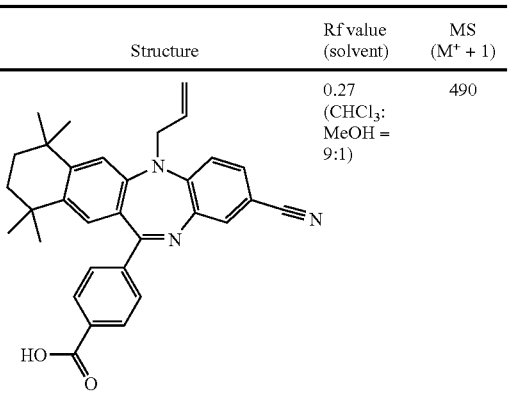

38

By repeating the procedures described above using appropriate starting materials and conditions, the following compounds are obtained.

| Example | Structure | Rf value (solvent) | MS (M$^+$ + 1) |
|---|---|---|---|
| 38 | 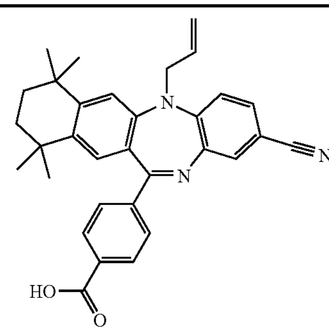 | 0.27 (CHCl$_3$: MeOH = 9:1) | 490 |

-continued

| Example | Structure | Rf value (solvent) | MS (M⁺ + 1) |
|---|---|---|---|
| 39 | 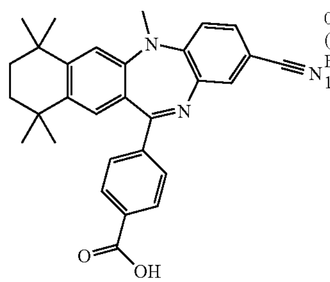 | 0.25 (Hexane: EtOAc = 1:3) | 464 |
| 40 | 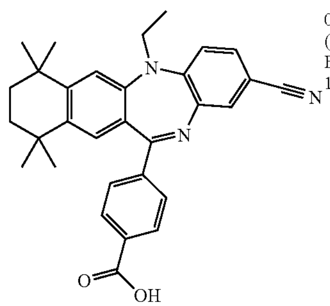 | 0.30 (Hexane: EtOAc = 1:3) | 478 |
| 41 | 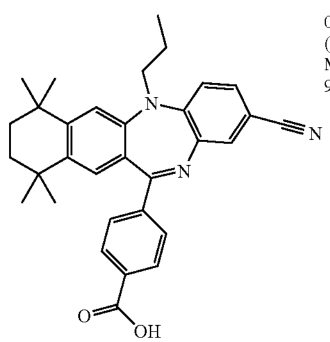 | 0.43 (CH₂Cl₂: MeOH = 9:1) | 492 |
| 42 | 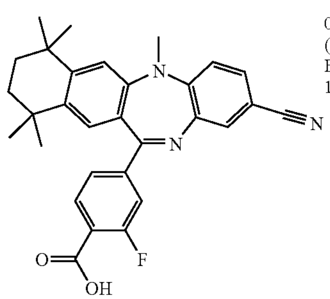 | 0.24 (Hexane: EtOAc = 1:5) | 482 |
| 43 | 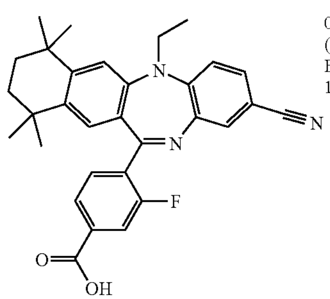 | 0.21 (Hexane: EtOAc = 1:5) | 496 |

What is claimed is:

1. A compound of formula (I) or a pharmaceutically acceptable salt thereof,

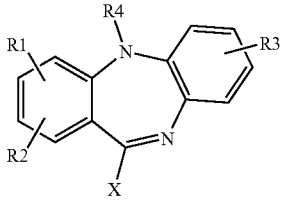

(I)

wherein R1 and R2, independently of each other, represent hydrogen, or $C_1$-$C_7$-alkyl, or R1 and R2 together with the carbon atoms of the phenyl ring to which they bind form a 5-, 6- or 7-membered cycloalkyl ring, which ring may optionally be substituted by one or more $C_1$-$C_7$-alkyl groups, which alkyl groups may also together form one or more 3-, 4-, 5-, 6- or 7-membered rings; R3 represents —CN, —CO— $R_5$, or hydrogen, provided that, if R3 is hydrogen, R4 must represent $C_3$-$C_7$-alkenyl or $C_3$-$C_7$-alkynyl; $R_5$ represents aryl, or alkyl being unsubstituted or substituted by halogen, cyano, nitro, hydroxy, $C_1$-$C_7$-alkoxy, carboxyl or aryl; R4 represents $C_1$-$C_7$-alkyl, $C_2$-$C_7$-alkenyl or $C_2$-$C_7$-alkynyl or R4 represents $C_2$-$C_7$-alkanoyl; and X represents ligand (a),

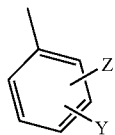

(a)

wherein Y may be in ortho, meta or para position and wherein Y represents carboxyl, $C_1$-$C_7$-alkoxy-carbonyl, aryloxycarbonyl, tetrazolyl, $SO_3H$ or $P(O)(OH)_2$; and wherein Z represents hydrogen or a substituent selected from the group consisting of $C_1$-$C_7$-alkyl, $C_1$-$C_7$-alkoxy, halogen, $CF_3$, cyano and $NO_2$.

2. Compound of claim 1, or a pharmaceutically acceptable salt thereof, wherein R1 and R2 are positioned as illustrated in formula (IIa)

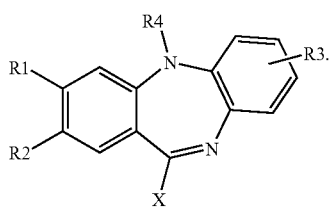

(IIa)

3. Compound of claim 1, or a pharmaceutically acceptable salt thereof, of formula (IIb)

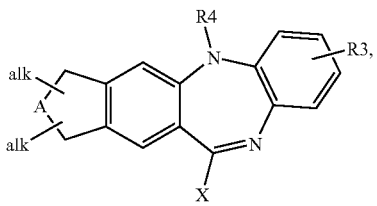

(IIb)

wherein alk in each case represent $C_1$-$C_7$-alkyl and A is $CH_2$, $CH_2CH_2$, or $CH_2CH_2CH_2$.

4. Compound of claim 1, or a pharmaceutically acceptable salt thereof, of formula (IIc)

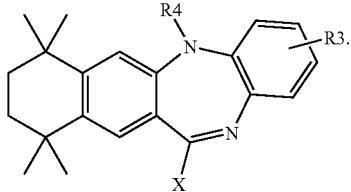

(IIc)

5. Compound of claim 1, or a pharmaceutically acceptable salt thereof, wherein X represents p-carboxyphenyl.

6. Compound of claim 1, or a pharmaceutically acceptable salt thereof, wherein R1 and R2 together with the two carbon atoms on the phenyl ring to which R1 and R2 respectively bind form 5,5,8,8-tetramethyl-5,6,7,8-tetrahydronaphthalene ring; X represents 4-carboxy-phenyl; R3 is cyano or $C_2$-$C_5$-alkanoyl; and R4 represents $C_1$-$C_7$-alkyl; $C_2$-$C_7$-alkenyl or $C_2$-$C_7$-alkynyl.

7. Compound of claim 6, or a pharmaceutically acceptable salt thereof, wherein for R3 is in the para-position relative to N—R4 in formula (I).

8. Compound of claim 6, or a pharmaceutically acceptable salt thereof, wherein R4 represents $C_1$-$C_7$-alkyl.

9. A pharmaceutical composition comprising a compound of claim 1, or a pharmaceutically acceptable salt thereof, in association with a pharmacologically and pharmaceutically acceptable additive.

10. Compound of claim 6, wherein R4 represents methyl or ethyl.

* * * * *